United States Patent
Wiglusz et al.

(10) Patent No.: US 11,180,370 B2
(45) Date of Patent: Nov. 23, 2021

(54) NANOCRYSTALLINE CALCIUM HYDROXYAPATITES, METHOD FOR ITS MANUFACTURE AND USE THEREOF IN REGENERATIVE MEDICINE AND THERANOSTIC

(71) Applicant: INSTYTUT NISKICH TEMPERATUR I BADAN STRUKTURALNYCH PAN IM.W.TRZEBIATOWSKIEGO, Wroclaw (PL)

(72) Inventors: Rafal Wiglusz, Wroclaw (PL); Krzysztof Marycz, Trzebinia (PL)

(73) Assignee: INSTYTUT NISKICH TEMPERATUR I BADAN STRUKTURALNYCH PAN IM.W.TRZRBIATOWSKIEGO, Wroclaw (PL)

(*) Notice: Subject to any disclaimer, the term of this patent is extended or adjusted under 35 U.S.C. 154(b) by 708 days.

(21) Appl. No.: 16/072,640

(22) PCT Filed: Jan. 25, 2017

(86) PCT No.: PCT/PL2017/050004
§ 371 (c)(1),
(2) Date: Jul. 25, 2018

(87) PCT Pub. No.: WO2017/131540
PCT Pub. Date: Aug. 3, 2017

(65) Prior Publication Data
US 2021/0206639 A1    Jul. 8, 2021

(30) Foreign Application Priority Data

Jan. 25, 2016 (PL) ..................................... P.415896
Apr. 21, 2016 (PL) ..................................... P.416922

(51) Int. Cl.
*A61K 35/30*     (2015.01)
*A61L 27/12*     (2006.01)
(Continued)

(52) U.S. Cl.
CPC .............. *C01B 25/45* (2013.01); *A61K 35/30* (2013.01); *A61L 27/12* (2013.01); *C12N 5/0622* (2013.01);
(Continued)

(58) Field of Classification Search
CPC .. A61L 27/12; A61L 2400/12; C01P 2002/52; A61K 6/75; A61K 6/838; A61K 6/842; A61K 49/0093; C01D 15/00
See application file for complete search history.

(56) References Cited

U.S. PATENT DOCUMENTS 4,097,935 A  *  7/1978  Jarcho ..................... A61K 6/17
                                                              623/23.61

FOREIGN PATENT DOCUMENTS

WO     2014/141287 A1     9/2014

OTHER PUBLICATIONS

Badran et al. (Radiation Physics and Chemistry 2017;130:85-91) (Year: 2017).*

(Continued)

*Primary Examiner* — Ernst V Arnold
(74) *Attorney, Agent, or Firm* — Maier & Maier, PLLC

(57) ABSTRACT

A method of manufacturing the calcium nanohydroxyapatite $Ca_{10}(PO_4)_6(OH)_2$ structurally modified with $Li^+$ ions (nHAP:$Li^+$) $Li_{0.1}Ca_{9.9}(PO_4)_6(OH)_2$ optionally doped with 1-2% mol of $Eu^{3+}$ cations in the form of nanocrystalline powder and use of $Li_{0.1}Ca_{9.9}(PO_4)_6(OH)_2$ in regenerative medicine as an agent improving of proliferative activity of progenitor cells and demonstrating an anti-apoptotic effect on progenitor cells and in addition use of $Li_{0.1}Ca_{9.9}(PO_4)_6$ $(OH)_2$ doped with 1-2% mol $Eu^{3+}$ cations as an agent improving of proliferative activity of progenitor cells and demonstrating the luminescence signal used in diagnostic application.

3 Claims, 16 Drawing Sheets

Specification includes a Sequence Listing.

(51) Int. Cl.
   *C01B 25/45* (2006.01)
   *C12N 5/079* (2010.01)
(52) U.S. Cl.
   CPC ....... *A61L 2400/12* (2013.01); *C01P 2002/52* (2013.01); *C01P 2002/72* (2013.01); *C01P 2002/82* (2013.01); *C01P 2004/03* (2013.01); *C01P 2004/04* (2013.01); *C01P 2004/16* (2013.01); *C01P 2004/64* (2013.01); *C01P 2006/12* (2013.01); *C12N 2500/14* (2013.01)

(56) References Cited

OTHER PUBLICATIONS

Bracken et al., "Methylprednisolone or naloxone treatment after acute spinal cord injury: 1-year follow-up data", J. Neurosurg, vol. 76, Jan. 1992, pp. 23-31.
Bracken et al., "Methylprednisolone or tirilazad mesylate administration after acute spinal cord injury: 1-year follow-up data", J. Neurosurg, vol. 89, Nov. 1998, pp. 699-706.
Chou et al., "The Potential Therapeutic Applications of Olfactory Ensheathing Cells in Regenerative Medicine", Cell Transplantation, vol. 23, Jan. 30, 2014, pp. 567-571.
Grosu-Bularda et al., "The role of olfactory ensheating cells in regenerative medicine: review of the literature", Romanian Journal of Rhinology, vol. 5, No. 18, Apr.-Jun. 2015, pp. 75-80.
Dasari et al., "Mesenchymal stem cells in the treatment of spinal cord injuries: A review", World Journal of Stem Cells, vol. 6, Issue 2, Apr. 26, 2014, pp. 120-133.
Tabakow et al., "Transplantation of Autologous Olfactory Ensheathing Cells in Complete Human Spinal Cord Injury", Cell Transplantation, vol. 22, Apr. 2, 2013, pp. 1591-1612.
Lu et al., "Olfactory ensheathing cells promote locomotor recovery after delayed transplantation into transected spinal cord", Brain, vol. 125, 2002, pp. 14-21.
Li et al., "Cell Transplantation for Spinal Cord Injury: A Systematic Review", BioMed Research International, vol. 2013, Article ID 786475, Dec. 11, 2012, pp. 1-32.
Maizumi et al., "Transplanted Olfactory Ensheathing Cells Remyelinate and Enhance Axonal Conduction in the Demyelinated Dorsal Columns of the Rat Spinal Cord", The Journal of Neuroscience, vol. 18, No. 16, Aug. 15, 1998, pp. 6176-6185.
Moore et al., "Neuronal Differentiation of Adipose Derived Stem Cells: Progress So Far", International Journal of Photoenergy, vol. 2014, Article ID 827540, Jun. 30, 2014, pp. 1-8.
Bae et al., "Neuron-Like Differentiation of Bone Marrow-Derived Mesenchymal Stem Cells", Yonsei Med J, vol. 52, No. 3, 2011, pp. 401-412.
Ivanov et al., "Synthetic materials used for the substitution of bone defects", Critical Review, Annals of Oral & Maxillofacial Surgery, vol. 1, Feb. 1, 2013, pp. 1-4.
Ferraz et al., "Hydroxyapatite nanoparticles: A review of preparation methodologies", Journal of Applied Biomaterials & Biomechanics, vol. 2, 2004, pp. 74-80.
Liu et al., "Nanomedicine for implants: a review of studies and necessary experimental tools", Biomaterials, vol. 28, 2007, pp. 354-369.
Chandra et al., "A luminescent europium(III)-platinum(II) heterometallic complex as a theranostic agent: a proof-of-concept study", Dalton Transactions, vol. 45, 2016, pp. 494-497.
Venkatesan et al., "Combination of Nano-Hydroxyapatite with Stem Cells for Bone Tissue Engineering", Journal of Nanoscience and Nanotechnology, Aug. 9, 2016, pp. 8881-8894.
Dong et al., "Lithium enhanced cell proliferation and differentiation of mesenchymal stem cells to neural cells in rat spinal cord", Int J Clin Exp Pathol, vol. 8, No. 3, 2015, 2473-2483.
Hashimoto et al., "Lithium stimulates progenitor proliferation in cultured brain neurons", Neuroscience, vol. 117, 2003, pp. 55-61.
Wang et al., "Luminescent hydroxylapatite nanoparticles by surface functionalization", Applied Physics Letters, vol. 89, No. 183106, 2006, pp. 1-3.
Yang et al., "Bioactive, luminescent and mesoporous europium-doped hydroxyapatite as a drug carrier", Biomaterials, vol. 29, Aug. 19, 2008, pp. 4341-4347.
Queiroz et al. "Adsorption and release studies of sodium ampicillin from hydroxyapatite and glass-reinforced hydroxyapatite composites", Biomaterials, vol. 22, 2001, pp. 1393-1400.
Ravindranadh et al.,"Optical and structural properties of undoped and Mn2+ doped Ca—Li hydroxyapatite nanopowders using mechanochemical synthesis", Journal of Luminescence, vol. 159, 2015, pp. 119-127.
Martin et al., "Mechanisms involved in thermal diffusion of rare earth elements in apatite", Journal of Nuclear Materials, Elsevier, vol. 27, 1999, pp. 268-276.
Su et al., "Lithium enhances proliferation and neuronal differentiation of neural progenitor cells in vitro and after transplantation into the adult rat spinal cord", Experimental Neurology, vol. 206, 2007, pp. 296-307.
Sandhofer et al., Synthesis and preliminary in vivo evaluation of well-dispersed biomimetic nanocrystalline apatites labeled with positron emission tomographic imaging agents, Applied Materials & Interfaces, vol. 7, 2015 pp. 10623-10633.
Rietveld, "A profile refinement method for nuclear and magnetic structures", J. Appl .Cryst., vol. 2, 1969, pp. 65-71.
Wiglusz et al., "Synthesis and optical properties of Eu3+ ion doped nanocrystalline hydroxyapatites", Spectroscopy Letters, vol. 43, No. 5, Jul. 30, 2010, pp. 333-342.
Destainville et al., "Synthesis, characterization and thermal behavior of apatitic tricalcium phosphate", Materials Chemistry and Physics, vol. 80, 2003, pp. 269-277.
Abdulrahman et al., "From Garbage to Biomaterials: An Overview on Egg Shell Based Hydroxyapatite", Journal of Materials, vol. 2014, Article ID 802467, 2014, pp. 1-6.
Gibson et al., "Novel synthesis and characterization of an AB-type carbonate-substituted hydroxyapatite", J. Biome. Res., vol. 59, 2002, pp. 697-708.
Kokubo et al, "Novel bioactive materials with different mechanical properties", Biomaterials, vol. 24, 2003, pp. 2161-2175.
Kovaleva et al., "Bioresorbable carbonated hydroxyapatite Ca10-xNax(PO4)6-x(CO3)x(OH)2 powders for bioactive materials preparation", Central European Journal of Chemistry, vol. 7, No. 2, 2009, pp. 168-174.
Filippov et al., "Carbonate substituted hydroxyapatite (CHA) powder consolidated at 450°C", Journal of Physics Conference Series 291, 2011, 012036, pp. 1-8.
Grzesiak et al., "Characterization of Olfactory Ensheathing Glial Cells Cultured on Polyurethane/Polylactide Electrospun Nonwovens", International Journal of Polymer Science, vol. 2015, Article 908328, 2015, pp. 1-10.
Marycz et al., "Equine metabolic syndrome affects viability, senescence, and stress factors of equine adipose-derived mesenchymal stromal stem cells: New insight into EqASCs isolated from EMS horses in the context of their aging", Oxidative Medicine and Cellular Longevity, vol. 2016, Article ID 4710326, pp. 1-17.
Glant et al., "Bone resorption activity of particulate-stimulated macrophages", Journal of Bone and Mineral Research, vol. 8, No. 9, 1993, pp. 1071-1079.
Grzesiak et al., "Polyurethane/polylactide-based biomaterials combined with rat olfactory bulb-derived glial cells and adipose-derived mesenchymal stromal cells for neural regenerative medicine applications", Materials Science and Engineering C, vol. 52, 2015, pp. 163-170.
Dominici et al.,"Minimal criteria for defining multipotent mesenchymal stromal cells. The International Society for Cellular Therapy position statement", Cytotherapy, vol. 8, 2006, pp. 315-317.
Mayeur et al., "Potential of Olfactory Ensheathing Cells from Different Sources for Spinal Cord Repair", PLOS One, vol. 8, Issue 4, Apr. 2013, pp. 1-12.

(56) References Cited

OTHER PUBLICATIONS

Zanni et al., "Lithium increases proliferation of hippocampal neural stem/progenitor cells and rescues irradiation-induced cell cycle arrest in vitro", Oncotarget, vol. 6, No. 35, Sep. 8, 2015, pp. 37083-37097.

Yoneyama et al., Lithium Promotes Neuronal Repair and Ameliorates Depression-Like Behavior following Trimethyltin-Induced Neuronal Loss in the Dentate Gyrus, PLOS One, vol. 9, Issue 2, Feb. 2014, pp. 1-9.

Chen et al., "Long Term Lithium Treatment Suppresses p53 and Bax Expression but Increases Bcl-2 Expression", The Journal of Biological Chemistry, vol. 274, Issue of Mar. 5, 1999, pp. 6039-6042.

Ghasemi-Mobarakeh et al., "Structural properties of scaffolds: Crucial parameters towards stem cells differentiation", World Journal of Stem Cells, vol. 7, Issue 4, May 26, 2015, pp. 728-744.

Tchao et al., "Combined biophysical and soluble factor modulation induces cardiomyocyte differentiation from human muscle derived stem cells", Scientific Reports, vol. 4, 2014, p. 1-11.

Kempen et al., "Theranostic Mesoporous Silica Nanoparticles Biodegrade after Pro-Survival Drug Delivery and Ultrasound/Magnetic Resonance Imaging of Stem Cells", Theranostics, vol. 5, Issue 6, Mar. 1, 2015, pp. 631-642.

Tsintou et al., "Advances in regenerative therapies for spinal cord injury: a biomaterials approach", Neural Regeneration Research, vol. 10, Issue 5, May 2015, pp. 726-742.

International Search Report and Written Opinion dated Aug. 14, 2017 in corresponding International Application No. PCT/PL2017/050004; 5 pages.

Koutsoukos et al., "The Effect of Lithium on the Precipitation of Hydroxyapatite from Aqueous Solutions", Colloids and Surfaces, vol. 17, No. 4, Apr. 1, 1986, pp. 361-370.

Kaygili et al., "Synthesis and characterization of lithium calcium phosphate ceramics", Cermaics International, vol. 39, No. 7, Mar. 20, 2013, pp. 7779-7785.

Doubling Time Online Computing, URL: http://www.doubling-time.com/compute.php.

\* cited by examiner

A

B

C

D

NANOCRYSTALLINE CALCIUM HYDROXYAPATITES, METHOD FOR ITS MANUFACTURE AND USE THEREOF IN REGENERATIVE MEDICINE AND THERANOSTIC

The object of the invention is a nanocrystalline calcium hydroxyapatites, method for its manufacture and use thereof in regenerative medicine and theranostic.

BACKGROUND

Tissue engineering is a field dedicated to the use of medical knowledge and methods of material science to produce functional replacements for damaged tissues and organs. However, regeneration of central nervous tissue is limited. Therefore, it's injuries (e.g. traffic or sport accidents) are encumbered by a reduced healing probability that can be the reason for significant clinical problems associated with long-lasting treatment and lack of patient's comfort during the overall treatment process. Moreover, damages associated with trauma often requires simultaneous healing of nervous and bone tissues. Hence, the stimulation of neurogenesis can offer potential implements for replacing neurons. Medically approved procedures are only limited for patients that suffer from incomplete spinal cord injury (SCI) [1,2]. Application of cellular components, connected with bridging, pro-regenerative and biodegradable materials seems to be absolutely crucial and necessary. Recently, much attention has been paid to a unique population of progenitor cells—olfactory ensheathing cells (OECs) and mesenchymal stromal cells—successfully used in a patient with total spinal cord injury [3,4,5].

Beneficial effect of the OECs in regeneration of central nerve system in human was excellently shown by Tabakow and colleagues [6]. The OECs belong to macroglia, existing in lamina propria of olfactory mucosa, around the olfactory nerve fascicles, and in the two outer layers of the olfactory bulb. In turn, glial cells are present within the outer layers of olfactory bulb and possess the ability to support neural and glial cell differentiation, most importantly re-growth of severed long neural tracts. Unique regenerative features of this population of cells boils down to stimulation of central axon and peripheral nerve re-growth [7]. It has been showed, that OECs transplanted into complete transection lesions of the thoracic spinal cord of rats, enhances axons regeneration with simultaneous restoring of previously paralyzed limbs [8,9].

The application of mesenchymal stromal cells (MSCs) for cellular repair after central nervous system (CNS) injuries is another promising therapeutic solution [5][5]. The mesenchymal stromal cells are multipotent cells, residing in adult organism and capable to differentiate into cells forming bone, cartilage and adipose tissue, however the high cellular plasticity of this population is also expressed by their ability to differentiate into neural-like cells [10]. Neuronal differentiation of MSCs was confirmed for two, well-described lineages derived from bone marrow and adipose-tissue i.e. BMSCs and ASCs, respectively [11]. The features of ASCs that makes them favourable source of neural progenitor cells for SCI are mainly, high proliferative and secretory activity, high cellular plasticity, but further—the ease of isolation and cryopreservation, along with the maintenance of viability and regenerative capacity after cryopreservation at −80° C. Another, special characteristic that improves therapeutic efficacy of transplants is the immunoregulatory capacity if ASCs, reflecting on minimal or no immunoreactivity and graft-versus-host reaction, therefore good clinical outcomes [5,10].

The results of cell-based therapies proposed for SCI are variable, as their strictly depend on proliferative and differentiation potential of progenitor cells. Functional outcomes of this therapies may be improved by bioactive scaffolds used not only as a delivery system for cells but also modulating cytophysiological behaviour of cells. Application of the specific biomaterial serving as a carrier enhancing proliferative activity and functionality of the progenitors in nerve tissue regeneration seems to be fairly reasonable.

Calcium hydroxyapatite (HAP), with the general chemical formula $Ca_{10}(PO_4)_6(OH)_2$, is regarded as the most biocompatible compound widely used as a bone substitute material. The HAP can be obtained from several sources: autogenic (from patient), allogenic (human donor), xenogenic (animal donor) and synthetically [12,13]. Since naturally occurring HAP, in the bone tissue, exists in forms of nanostructures only such small objects can assure appropriate resorption/remineralization cycles and high affinity to the proteins being a vital feature for cells activity [14].

The novel trends in biomaterial and tissue engineering are aimed on theranostic application of scaffold-based and cell-based constructs [15]. This brings us closer to the personalized medicine, not only by the tailoring biomaterials physiochemical and biological features but also because of creating smart biomaterials targeting on drug delivery and real-time monitoring of treatment effect. This alternative would be extremely expected and feasible method for treatment modality for neuronal replacement and repair. However, nanosize HAP (hereinafter, nanohydroxyapatite or nHAP) is the most efficient for being used in bone repair in comparison with the microsize, because it stimulate tissue regeneration at the bone or implant interface [16].

It was shown in the prior art, that $Li^+$ cations enhance the proliferative ability of bone marrow stromal stem cells through GSK-3b-dependent b-catenin/Wnt pathway activation [17]. What is more important, lithium can stimulate the survival, proliferation and differentiation of neural progenitor cells [18]. Therefore, porous hydroxyapatite may serve as an ideal drug carrier for the delivery of a variety of pharmaceutical molecules [19,20,21].

The main technical problem is to provide the cost efficient way of manufacturing of nanohydroxyapatite in the form of biocompatible nanostructures which can be used for regenerative medicine and theranostic (diagnostic or therapy).

The mechanochemical method of manufacturing of nHAP doped with $Li^+$ ions was disclosed by Ravindranadh et all [22].

The substitution of the divalent calcium ion by trivalent rare earth ions ($RE^{3+}$) can be possible through the charge compensation mechanisms [23].

The aim of the invention is to provide method of manufacturing calcium nanohydroxyapatite structurally modified with $Li^+$ doping ions ($Ca_{10-x}Li_x(PO_4)_6(OH)_2$-nHAP:$Li^+$, where x-0-50 mol %) with biocompatibility and osteoconductivity and use thereof in regenerative medicine. In addition the aim of the invention is to provide nanostructure nanohydroxyapatite structurally modified with $Li^+$ ions (nHAP:$Li^+$) doped with $Eu^{3+}$ ions (europium (III) and use thereof in theranostic.

To balance the charge of lanthanide ion the use of monovalent $Li^+$ cations is provided that stimulate the survival, proliferation and differentiation of neural progenitor cells used for the treatment of damaged spinal cord [24]. It is noted that such actions could lead to the strengthening of luminescence and therefore might be used in diagnostic or therapy—theranostic [25].

SUMMARY

The first object of the invention is the method of manufacturing the calcium nanohydroxyapatite $Ca_{10}(PO_4)_6(OH)_2$ structurally modified with $Li^+$ ions ($nHAP:Li^+$) $Li_{0.1}Ca_{9.9}(PO_4)_6(OH)_2$ optionally doped with 1-2% mol of $Eu^{3+}$ cations in the form of nanocrystalline powder according to the invention characterized in that it consists of seventh steps, where:

in a first step the water soluble lithium nitrate is obtained by digestion of the stoichiometric amount of $Li_2CO_3$ in an excess of $HNO_3$;

in a second step depending on the final product which is obtained the solution of water soluble calcium nitrate is obtained by suspension of 73.35 g of $Ca(OH)_2$ in 200 ml of deionized water and subsequent digestion of calcium dioxide in an excess of 65% $HNO_3$ and 170 g of polyvinylpyrrolidone is added or the pure europium (III) nitrate is obtained by suspending stoichiometric amounts 0.0352 g of $Eu_2O_3$ in distilled water and subsequent digestion of europium oxide in an excess of 65% $HNO_3$ and subsequent three times re-crystallization and solution of 2.2434 g of $Ca(NO_3)_2.4H_2O$ dissolved in MQ-water (MiliQ water or distilled water) is added in a third step the ammonium phosphate solution is obtained by dissolution of $(NH_4)_2HPO_4$ in water in a fourth step solutions prepared in the steps 1-2 are added to the ammonium phosphate solution obtained in step 3, leading to fast precipitation of the by-product in a fifth step the pH is adjusted to 8-10 by addition of ammonium hydroxide $NH_4OH$ and the mixture is filtrated under reduced pressure in a sixth step the precipitate resulted in step 5 is washed 5 times and dried at 90° C. for 20-24 h in a seventh step the precipitate resulted in step 6 is subjected to a thermal treatment by gradually heating at 400-500° C. in air atmosphere for 3-4 hours, at a heating rate of 5° C. per minute to obtain final product.

Preferably, the method according to the invention is characterized in that for manufacturing of $Li_{0.1}Ca_{9.9}(PO_4)_6(OH)_2$ in the seventh step the precipitate resulted in step 6 is subjected to a thermal treatment by gradually heating at 400° C. in air atmosphere for 4 hours, at a heating rate of 5° C. per minute to obtain final product with the particle size distribution in the range of 30-50 nm and surface area 40 $m^2/g$ or gradually heating at 500° C. in air atmosphere for 8 hours, at a heating rate of 20° C. per minute to obtain particle size distribution in the range of 50-80 nm and surface area 30 $m^2/g$.

Preferably, the method according to the invention is characterized in that for manufacturing of for manufacturing $Li_{0.1}Ca_{9.9}(PO_4)_6(OH)_2$ doped with 1-2% mol of $Eu^{3+}$ in the step seventh the precipitate resulted in step 6 is subjected to a thermal treatment by gradually heating at 500° C. in air atmosphere for 3 hours, at a heating rate of 5° C. per minute to obtain fine graded white powder with elongated rod-like shape particles with mean particle size being of 80 nm length and 15 nm width.

The method for manufacturing of calcium nHAP structurally modified with $Li^+$ ions, optionally doped with with 1-2% mol of $Eu^{3+}$ according to the invention is simple, accessible and uses readily available components of natural origin.

Second object of the invention is the use of $Li_{0.1}Ca_{9.9}(PO_4)_6(OH)_2$ manufactured as described above in regenerative medicine as an agent improving of proliferative activity of progenitor cells and demonstrating an anti-apoptotic effect on progenitor cells.

Another object of the invention is the use of $Li_{0.1}Ca_{9.9}(PO_4)_6(OH)_2$ doped with 1-2% mol $Eu^{3+}$ cations manufactured as described above as an agent improving of proliferative activity of progenitor cells and demonstrating the luminescence signal used in diagnostic application.

To examine the proliferative and ani-apoptotic activity of compound according to the invention the stromal stem cell as well as olfactory ensheathing cells were used hOECs and hASCs.

The novel biomaterials manufactured according to the invention could find application in regenerative medicine as well as diagnostic application, especially in the field of spinal cord injuries treatment. The presented methodology of biomaterials synthesis and evaluation is repeatable.

The wet chemistry method followed by heat treatment at 500° C. has been developed to synthesize $Li^+$ ions doped and $Eu^{3+}$ co-doped hydroxyapatite nanoparticles. The physicochemical analysis has shown that $Li^+$ as well as $Eu^{3+}$ ions have been successfully incorporated into the hydroxyapatite structure. The results reveal that the obtained materials are well assigned to the hexagonal lattice structure of the hydroxyapatite phase. The concentration of $Li^+$ ions was 5 mol % and $Eu^{3+}$ were 1 and 2 mol %. The nano-nature of the final product was confirmed by different technique of grain size calculation and TEM images, showing the particles are of regular, elongated rod-like shapes with mean particle size being of 80 nm length and 15 nm width. Moreover, the $Li^+$ ions released from the nanohydroxyapatites was detected showing the quick release of $Li^+$ lasts over one and a half hour until the system starts to slowly achieve its equilibrium and this second stage lasts for more than 17 hrs.

Obtained biomaterials revealed proper biocompatibility, the pro-proliferative and pro-survival effect of $nHAP:Li^+$ was confirmed. Both physicochemical as well as biological properties of obtained materials predestines for regenerative and diagnostic medicine application. Additional, so-called co-doping with europium(III) ions ($nHAP:Li^+,Eu^{3+}$) caused improvement of proliferative activity of progenitor cells and what is more allowed to record luminescence signal, that might be used in future in theranostic application.

The invention is explained in detail in embodiments that do not limit its scope.

BRIEF DESCRIPTION OF THE DRAWINGS

The invention is illustrated in the drawing, where.

DETAILED DESCRIPTION

Example 1

Figure 1:
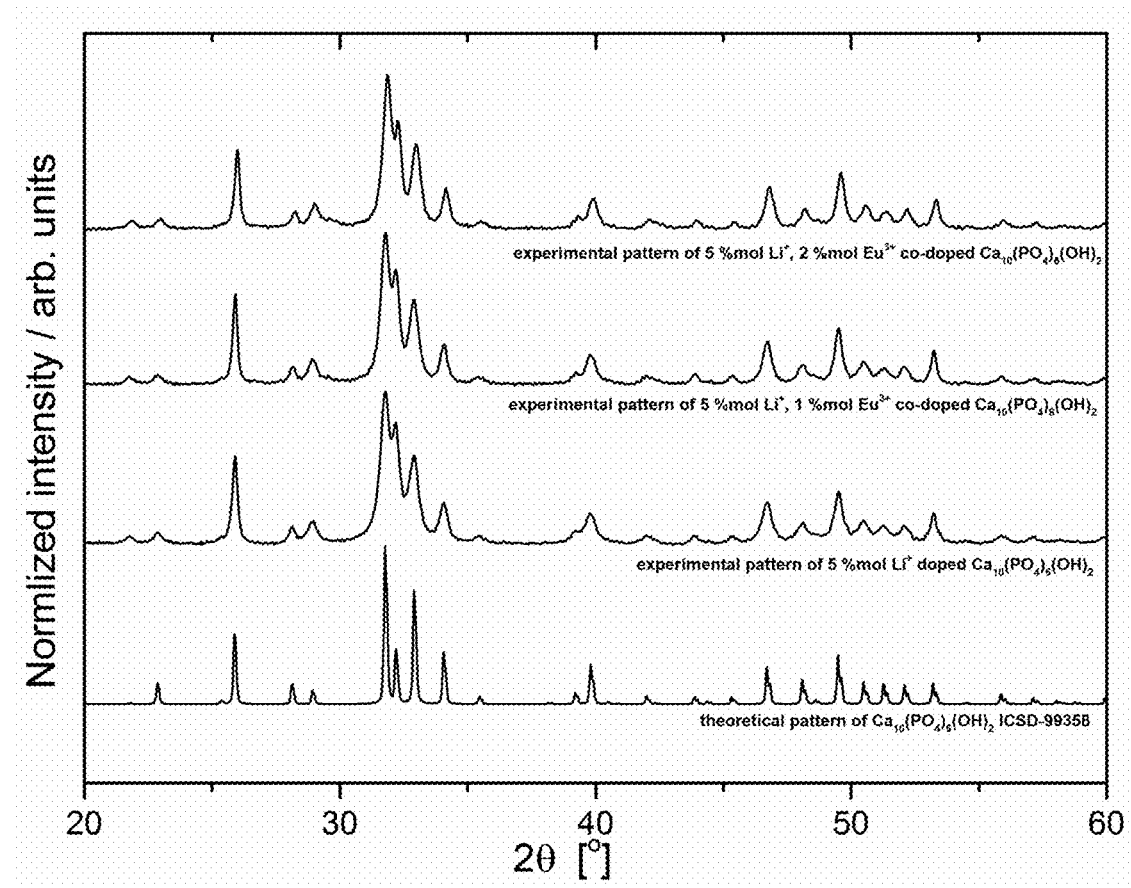
FIG. 1 presents the results of the XRD measurement of all obtained samples and Rietveld refinement [26] of the nHAP: $Li^+$ powders.
Figure 2:
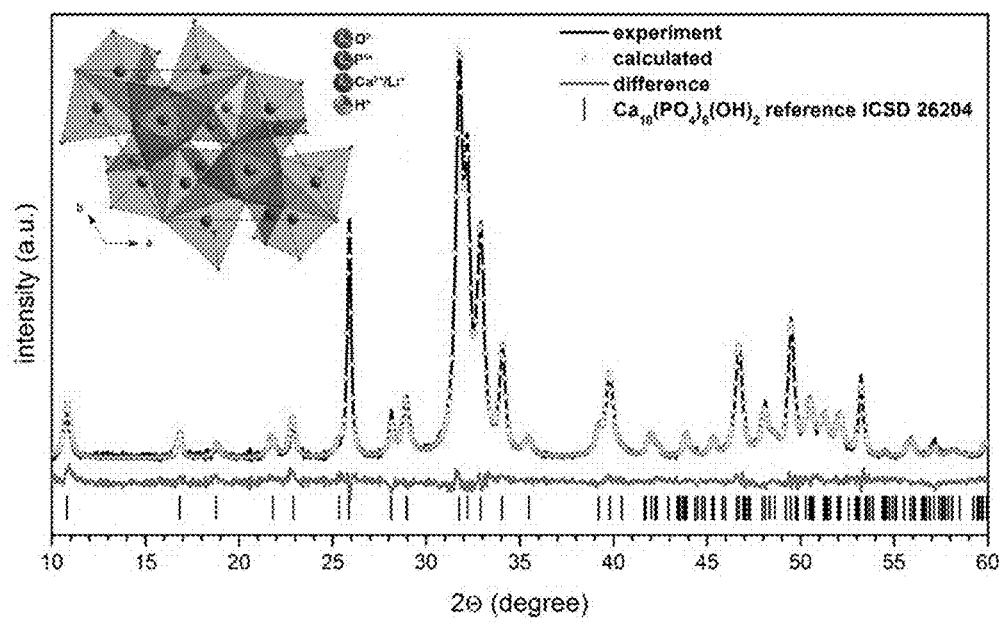
FIG. 2 presents the result of the Rietveld analysis of the nHAP doped with 5 mol % $Li^+$ heated at 500° C. (taking a view from the line located at the lowest position of an axis intensity in an upper direction), the column are the reference phase peaks position of $Ca_{10}(PO_4)_6(OH)_2$, the grey line is differential pattern, the black line refers to XRD pattern, partially covered with grey pattern which is fitted diffraction line.

Calcium nanohydroxyapatite $Ca_{10}(PO_4)_6(OH)_2$ structurally modified with Li$^+$ ions (nHAP:Li$^+$) $Li_{0.1}Ca_{9.9}(PO_4)_6(OH)_2$ in the form of nanocrystalline powder is obtained in a multi-step process, in replacement of overall molar content of $Ca^{2+}$ ions. Analytical grade calcium hydroxide $Ca(OH)_2$ (99% Acros Organics), diammonium phosphate $NH_4H_2PO_4$ (99.995% Alfa Aesar), lithium carbonate $Li_2CO_3$ (99.9% Alfa Aesar), 65% nitric acid $HNO_3$ (ultrapure Avantor Poland) and ammonium hydroxide $NH_4OH$ (99% Avantor Poland) for pH adjustment were used.

On the scale was weighed in sequence 73.35 g calcium hydroxide $Ca(OH)_2$ (analytical grade 99% Acros Organics), 79.234 g diammonium phosphate $(NH_4)_2HPO_4$ (99.995% Alfa Aesar), and 0.37 g lithium carbonate $Li_2CO_3$ (99.9% Alfa Aesar). All substances were placed into three separate beakers.

At first, the stoichiometric amount of the $Li_2CO_3$ was digested in an excess of $HNO_3$ (65% ultrapure Avantor Poland) in order to transform lithium carbonate into the water soluble lithium nitrate.

Then the stoichiometric amounts of $Ca(OH)_2$ were suspended in 200 ml of deionized water and digested with stirring in an excess of 138.5 ml nitric acid $HNO_3$ (65%, ultrapure Avantor Poland) to obtain water soluble calcium nitrates.

Subsequently, to a solution containing calcium nitrate, the final volume of about 340 ml, was added 170 g of polyvinylpyrrolidone (PVP) (50% relative to the weight of the calcium nitrate). In order to achieve complete dissolution of the PVP the process can be assisted by using a mechanical stirring and heating the mixture at 60° C. for 1 hour.

Then, the Afterwards, the solution was transferred to the beaker containing calcium nitrate and PVP.

Next, the stoichiometric amount of the $(NH_4)_2HPO_4$ was dissolved under vigorous stirring in an excess of 250 ml of $H_2O$ in order to obtain the ammonium phosphate solution. Finally, all previously prepared solutions of calcium nitrate, lithium nitrate and PVP were added to the mixture of ammonium phosphate leading to the fast precipitation of the by-product. In the last step, the pH of the dispersion was modulated to 8-9 by addition of ammonium hydroxide $NH_4OH$ (99% Avantor Poland). After two hours of vigorous stirring at room temperature the mixture was filtrated using a conventional laboratory filtration system under reduced pressure.

The supernatant was removed, and the precipitate of white by-products was transferred from the filter into a beaker and refined with distilled water and filtered, respectively. The washing step was repeated five times. The wet powder was transferred from the filter to the drying chamber and dried at 90° C. for 24 h.

Formation of $Li_{0.1}Ca_{9.9}(PO_4)_6(OH)_2$ with 30-50 nm Particle Size Distribution The calcium hydroxyapatite powder $Ca_{10}(PO_4)_6(OH)_2$ doped with 5 mol % of Li$^+$ ions in amount of 100 g was added into a crucible and then into a muffle furnace and was gradually heated at 400° C. in air atmosphere, at a heating rate of 5° C. per minute.

The thermal treatment at 400° C. for 4 hours was the last step during materials preparation in order to crystallize the $Li_{0.1}Ca_{9.9}(PO_4)_6(OH)_2$ with the particle size distribution in the range of 30-50 nm. The results of the high specific surface area using BET (Brunauer-Emmett-Teller) analysis of obtained powder was 40 m$^2$/g.

Formation of $Li_{0.1}Ca_{9.9}(PO_4)_6(OH)_2$ with 50-80 nm Particle Size Distribution The calcium hydroxyapatite powder $Ca_{10}(PO_4)_6(OH)_2$ doped with 5 mol % of Li$^+$ ions in amount of 100 g was added into a crucible and then into a muffle furnace and was gradually heated at 500° C. in air atmosphere, at a heating rate of 20° C. per minute.

The thermal treatment at 500° C. for 8 hours was the last step during materials preparation in order to crystallize the $Li_{0.1}Ca_{9.9}(PO_4)_6(OH)_2$ with the particle sized distribution in the range of 50-80 nm. The results of the high specific surface area using BET (Brunauer-Emmett-Teller) analysis of obtained powder was 30 m$^2$/g.

Example 2

Calcium nanohydroxyapatite $Ca_{10}(PO_4)_6(OH)_2$ structurally modified with 5% mol of Li+ ions (nHAP:Li$^+$) doped with 1-2% mol Eu$^{3+}$ cations in the form of nanocrystalline powder is obtained using co-precipitation technique.

Analytical grade calcium hydroxide $Ca(NO_3)_2 \cdot 4H_2O$ (99.98% Alfa Aesar), diammonium phosphate $NH_4H_2PO_4$ (99.99% Sigma Aldrich), lithium carbonate $Li_2CO_3$ (99% Alfa Aesar), $Eu_2O_3$ (99.99% Alfa Aesar), nitric acid $HNO_3$ (65% ultrapure Avantor Poland) and ammonium hydroxide $NH_4OH$ (99% Avantor Poland) for pH adjustment were used as the main substrates.

For preparation calcium nanohydroxyapatite structurally modified with 5% mol of Li$^+$ ions doped with 1% mol Eu$^{3+}$ cations, in the first step the water soluble lithium nitrate is obtained by digestion of the stoichiometric amount 0.185 g of $Li_2CO_3$ in an excess of $HNO_3$ (65% ultrapure Avantor Poland).

Subsequently, the pure europium (III) nitrate is obtained by suspending stoichiometric amounts 0.0352 g of $Eu_2O_3$ in distilled water and subsequent digestion of europium oxide in an excess of 65% $HNO_3$ and three times re-crystallization and solution of 2.2434 g of $Ca(NO_3)_2 \cdot 4H_2O$ dissolved in MQ-water is added In a third step the ammonium phosphate solution is obtained by dissolution of $(NH_4)_2HPO_4$ in water.

Afterwards together with $LiNO_3$ (obtained in the first step) and the pure europium (III) nitrate (obtained in the second step) subsequently 0.7923 g (6 mmol) of $(NH_4)_2HPO_4$ was added to the mixture resulting in a fast precipitation of the by-product. The solution pH was adjusted to 10 with $NH_4OH$ under constant and vigorous stirring at 90° C. for 4 hours. Finally, by-products were dried for 20 hrs at 90° C. and thermally treated at 500° C. for 3 hours resulting in formation of white, fine-grained powders.

The final product was the subject of high resolution transmission electron microscopy (HR-TEM) to confirm particle size and morphology. The HR-TEM shows, that particles of calcium nanohydroxyapatite $Ca_{10}(PO_4)_6(OH)_2$ structurally modified with 5% mol of Li$^+$ ions (nHAP:Li$^+$) doped with 1-2% mol Eu$^{3+}$ cations are of regular, elongated rod-like shapes with mean particle size being of 80 nm length and 15 nm width.

Example 3

The In Vitro Li$^+$ Release and its Determination

The $Ca_{10}(PO_4)_6(OH)_2$ containing 5 mol % of Li$^+$ obtained in accordance with Example 1 were transformed into the form of pellets by using mechanical press. Pellets were put into bottles filled with phosphate buffer (PBS, pH 7.4, 100 ml). Afterwards, samples were incubated at 37° C. under constant stirring at 150 rpm. Each time and with specific time intervals 0.5 ml of solution containing nHAP:Li$^+$ was withdrawn and diluted ten times with PBS and immediately replaced with 0.5 ml of fresh PBS medium. In that way a time dependent release study was carried out for 48 hours. Three independent measurements were carried out. Final determination of Li$^+$ was done by means of ICP OES (coupled plasma optical emission spectrometry) technique using the 6-point calibration curves covering the concentration range between 50-2000 µg/ml.

Example 4

The Physicochemical Characterization of nHAP:Li$^+$ and nHAP:Li$^+$, Eu$^{3+}$

The X-Ray Powder Diffraction and Rietveld Refinement

The ion(s)-release process in nHAP strongly depends on the particle size and crystallinity of the material. Small particles in contrast to larger counterparts are characterized by the extended surface area and therefore, better contact with outer surrounding allowing for more effective ions release. In order to prevent from instantaneous outburst of ionic species high crystallinity of HAP is crucial. In fact, both factors mentioned above are strongly related to each other and one has to find a balance between them. Thus, since the formation of crystalline phase of the HAP nanoparticles is well described in the literature [27], annealing temperature of 500° C. was chosen as the most adequate in terms of particle size and crystallinity.

As shown in FIG. 1 the nHAP:Li$^+$ powders exhibit a very good correspondence with the reference standard of the HAP hexagonal phase (ICSD 26204). The cell parameters (Table 1) were calculated using Rietveld method assuming incorporation of the Li$^+$ ions at both Ca$^{2+}$ sites (Ca(1) and Ca(2)) with even distribution between both cationic sites. The results of fitting leads to the final conclusion that nHAP:Li$^+$ nanoparticles are of high purity without presence of any other phases and lithium cations are incorporated in the crystal structure of the nanohydroxyapatite presents the results of the XRD measurement of all obtained samples and Rietveld refinement [28] of the nHAP:Li$^+$ powders.

TABLE 1

Atomic parameters of the $Ca_{10}(PO_4)_6(OH)_2$ doped with 5 mol % of Li$^+$ ions.

| Sample | $Ca_{10}(PO_4)_6 (OH)_2$: 5% Li$^+$; Z = 1 |
|---|---|
| Space group | Hexagonal P6$_3$/m (176) |
| Calculated cell parameters | a = 9.4306(24) Å |
|  | c = 6.8811(24) Å |
|  | V = 529.99(27) Å$^3$ |
| R$_w$ | 3.29% |
| R$_{wnb}$ | 3.06% |
| R$_{all}$ | 2.52% |

TABLE 1-continued

Atomic parameters of the $Ca_{10}(PO_4)_6(OH)_2$ doped with 5 mol % of $Li^+$ ions.

| | |
|---|---|
| $R_{nb}$ | 2.57% |
| $\sigma$ | 1.93% |
| Selected shortest contacts | |
| Ca\|Li—Li\|Ca | 3.9384(9) Å |
| Ca\|Li—O | 2.3933(5) Å |
| P—O | 1.5097(4) Å |
| Ca\|Li—O—Li\|Ca | 89.487(4)° |

| Atom | Wyckoff positions | X | y | z | $B_{iso}$ | Occ. (<1) |
|---|---|---|---|---|---|---|
| O1 | 6h | 0.3272 | 0.4837 | 0.25 | 0.023531 | |
| O2 | 6h | 0.5836 | 0.4650 | 0.25 | 0.025321 | |

TABLE 1-continued

Atomic parameters of the $Ca_{10}(PO_4)_6(OH)_2$ doped with 5 mol % of $Li^+$ ions.

| O3 | 12i | 0.3420 | 0.2567 | 0.06359 | 0.018173 | |
|---|---|---|---|---|---|---|
| P1 | 6h | 0.3992 | 0.3617 | 0.25 | 0.017356 | |
| Ca1/Li1 | 4f | 0.3332 | 0.6671 | 0.0043 | 0.09148 | |
| Ca2/Li2 | 6h | 0.2452 | 0.9917 | 0.25 | 0.06772 | |
| O4 | 4e | 0 | 0 | 0.1787 | 0.025 | 0.5 |
| H1 | 4e | 0 | 0 | 0.0695 | 0.014180 | 0.5 |

Fourier Transform Infrared Spectroscopy

Figure 3:
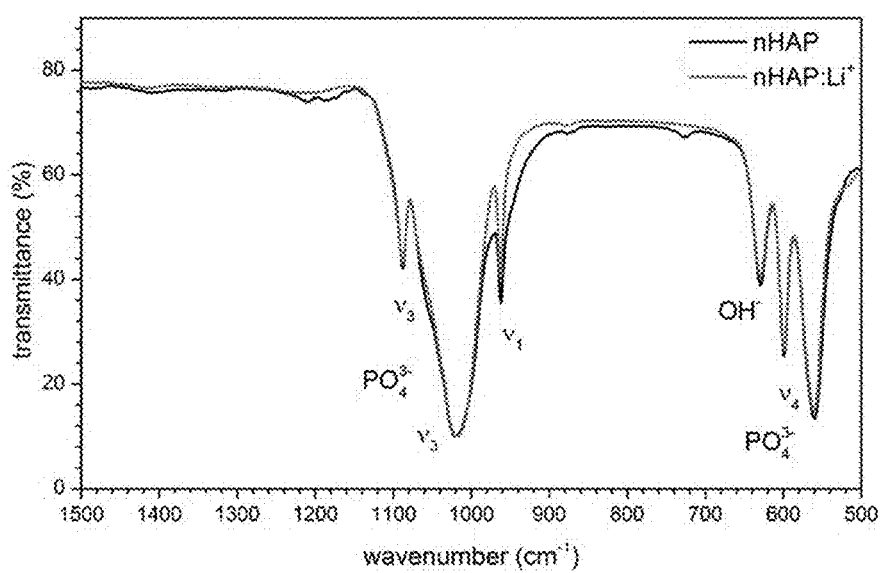
FIG. 3 presents the comparison of the FTIR spectra of pure nHAP (black line) with $nHAP:Li^+$ (grey line) nanoparticles.

The FT-IR spectra were recorded for purity and 5 mol % $Li^+$ doped nHAP nanoparticles covering the spectral region of 500-1200 cm$^{-1}$ at room temperature. The spectra (see FIG. 3) consists of typical vibrations of the $PO_4^{3-}$ groups at 598 cm$^{-1}$, 559 cm$^{-1}$ ($v_4$), 961 cm$^{-1}$ ($v_1$), 1088 cm$^{-1}$ and 1018 cm$^{-1}$ ($v_3$) as well as OH vibration mode at 630 cm$^{-1}$. In the case of pure nHAP one can individuate low intensity modes at 725 cm$^{-1}$ and 1200 cm$^{-1}$ usually attributed to the vibrations of the $P_2O_7^{4-}$ units connected with transformation of the $HPO_4^{2-}$. The last feature with low intensity is located at 875 cm$^{-1}$ and its source is usually seen in surface absorption of $CO_2$ from air or substitution of $PO_4^{3-}$ with $CO_3^{2-}$ groups [29]. These bands disappear completely upon doping with $Li^+$ except for the $CO_3^{2-}$ vibrations. The presence of small amount of carbonates is characteristic of biogenic hydroxyapatites and does not affect the final properties of the material [30]. Actually, the presence of $CO_3^{2-}$ is desirable since such composition approximates much better the inorganic part of natural bone tissue (up to 8 wt. %) [31,32] increasing bioresorbtion [33] due to the fact of existence of structural distortion induced by $CO_3^{2-}$ substitution [34].

HR-TEM Microscopy and SEM Elements Mapping

Figure 4:
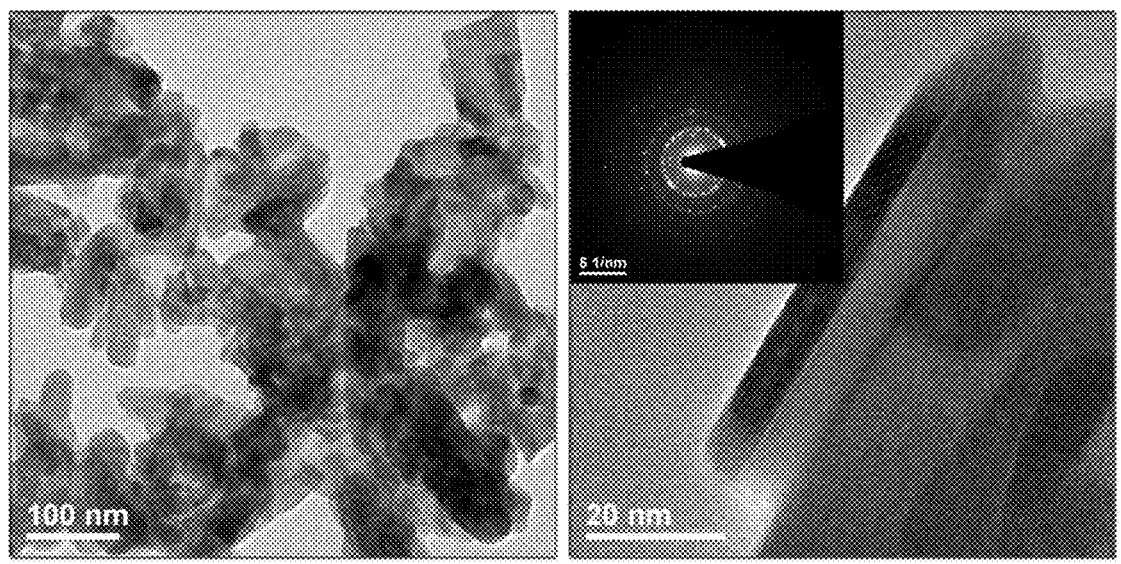
FIG. 4 presents TEM and SAED images of the nHAP: 5 mol % Li+ nanoparticles
Figure 5:
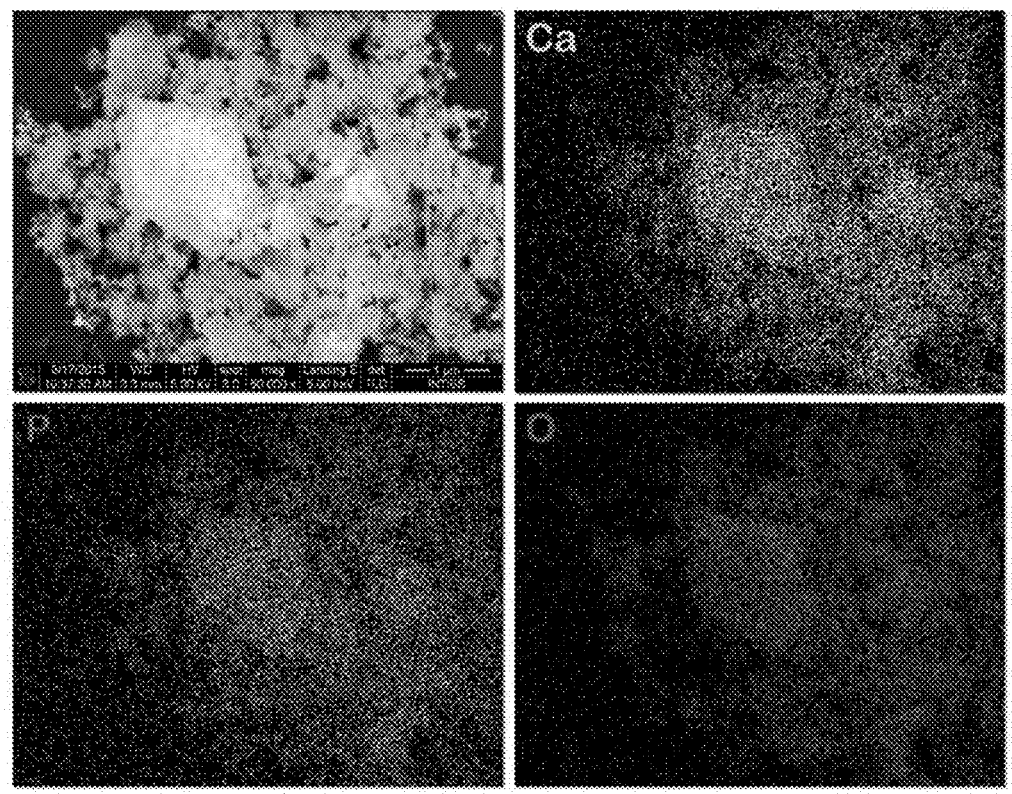
FIG. 5 presents SEM image and elements mapping (Ca, P and O) of the nHAP:Li$^+$ nanoparticles using SEM-EDS technique.

The final confirmation of particle size of the nHAP: 5 mol % $Li^+$ powder was done utilizing HR-TEM microscopy (see FIG. 4). In accordance with TEM one can note that the particles are of regular, elongated rod-like shapes with mean particle size being of 80 nm length and 15 nm width. Analysis of SAED pattern revealed appearance of well developed rings with clear reflections at positions corresponding with reference standard of calcium hydroxyapatite. Elements mapping and analysis was done using SEM-EDS microscopy (see FIG. 5) and ICP-OES technique (Table 2) in order to confirm the composition and homogenous distribution of the Ca, P and O. Lithium cations are to light to perform EDS analysis, therefore its content was confirmed directly by the ICP-OES analysis. All of the constituting elements were in a proper molar ratio confirming right stoichiometry of the final material. The ratio of the sum of $Ca^{2+}$ and $Li^+$ (since $Li^+$ was incorporated at Ca(I) and Ca(II) sites) cations to the $P^{5+}$ was 1.67 well matching with theoretical ratio of Ca/P in calcium hydroxyapatite.

TABLE 2

Representative results of the ICP-MS analysis of the nHAP: 5 mol % $Li^+$ nanoparticles.

| Sample mass (g) | Li (mg/ml) | Ca (mg/ml) | P (mg/ml) | Li (mol) | Ca (mol) | P (mol) | (Ca + Li)/P | Li/(Ca + Li)* 100% |
|---|---|---|---|---|---|---|---|---|
| 0.0923 | 3.6 | 356.3 | 173.7 | 0.0518 | 0.8890 | 0.5607 | 1.678 | 5.512 |
| | 3.67 | 356.9 | 175.6 | 0.0528 | 0.8905 | 0.5669 | 1.664 | 5.605 |
| | 3.53 | 355.7 | 171.8 | 0.0508 | 0.8875 | 0.5546 | 1.692 | 5.420 |
| | | | | | | Average | 1.678 | 5.51 |

$Li^+$ Time Release and its Concentration

Figure 6:
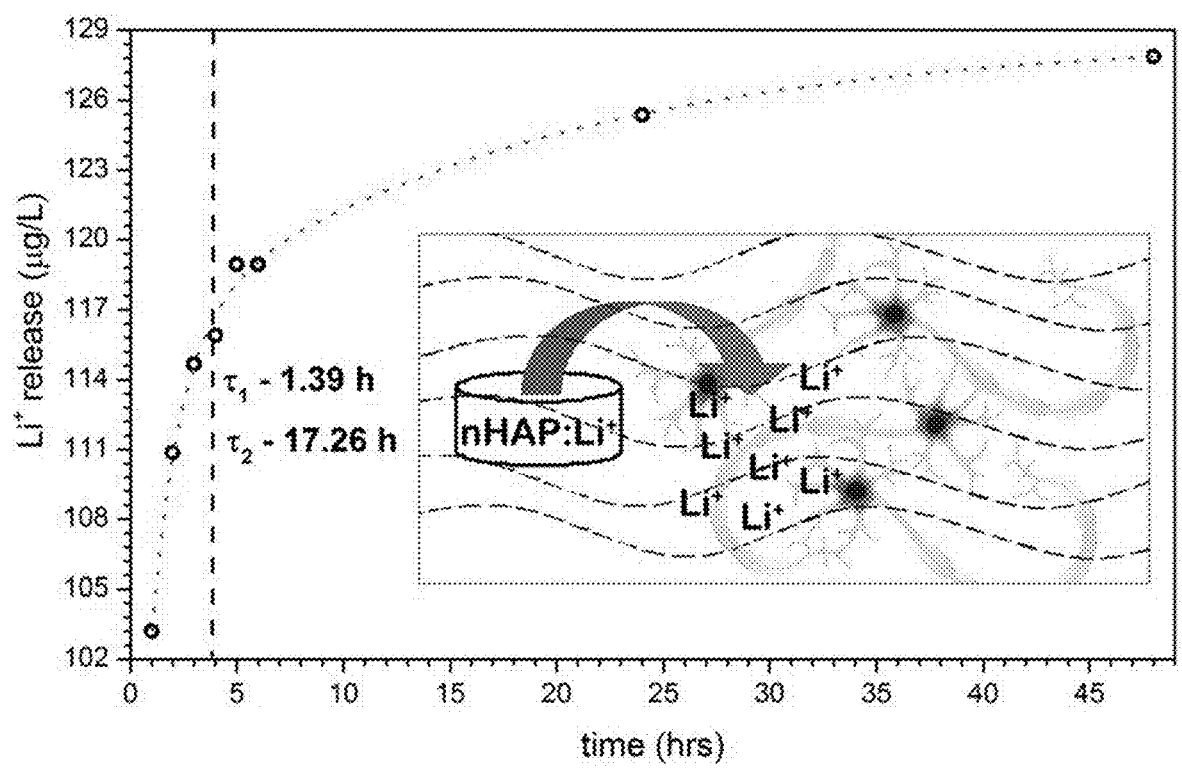
FIG. 6 presents time dependent release of Li+ cations from the nHAP: 5 mol % Li+ pellets immersed in PBS buffer medium.

Results of time dependent release study of the $Li^+$ from solid sample containing nanoparticles of the nHAP: 5 mol % $Li^+$ (see FIG. 6) can be divided into two main areas, the first one showing rather instantaneous release of the $Li^+$ cations after immersion in PBS buffer solution at pH 7.4 and the second one covering long-time region until the equilibrium concentration of the $Li^+$ is achieved in a given system. The curve was fitted using association exponential function showing that the quick release of $Li^+$ lasts over one and a half hour until the system starts to slowly achieve its equilibrium and this second stage lasts for more than 17 hrs. The most important fact is that once the nHAP:$Li^+$ sample is in contact with PBS solution the $Li^+$ cations are starting to resorb quickly and free Li+ cations can be detected with concentration of 117 μg/ml. Further release is limited by the equilibrium state keeping the constant concentration of $Li^+$ at 128 μg/ml in the solution in the steady system.

Example 5

The experiments were conducted with the approval of the Second Local Bioethical Commission at the Department of Biology and Animal Breeding, at University of Environmental and Life Sciences in Wroclaw, Chelmonskiego 38C, Poland (dec. number 177/2010 from 11.15.2010).

Isolation and characterization of human olfactory ensheathing glial cells (hOECs). Human olfactory bulbs and adipose tissues samples were collected post mortem from six healthy individuals (n=6), of average age 28±2 years, who died in traffic accidents. Olfactory bulb biopsies (~8 mm$^2$) were taken from the nasal septum in the superior region of the nasal cavity. The procedure of ensheathing glial cells isolation included: (i) washing of biopsies with Hank's balanced salt solution (HBSS); (ii) mincing with surgical scissors; (iii) incubation in collagenase solution (1 mg/mL, Sigma) for 10 min at 37° C. in $CO_2$ incubator. The olfactory bulb samples were additionally mechanically homogenized using syringe needles (18 G, 20 G and 22 G), according to the previously described protocol [35]. Enzymatic activity of collagenase was inhibited by the addition of complete growth medium (CGM) containing fetal bovine serum (DMEM F12/Ham's with 10% of FBS and 1% of penicillin/streptomycin/amphotericin b; all purchased from Sigma Aldrich). The obtained homogenate was centrifuged at 300×g for 3 min, and cell pellet was re-suspended in fresh CGM and placed in T-25 flasks with a seeding concentration equal $5 \times 10^3$ cells/cm$^2$. The cultures of hOECs were maintained in 37° C. 5% $CO_2$ humidified incubator for three days, then the medium was partially replaced (half of the medium volume was discarded and replaced with a fresh one), and cells were cultured for the next 2 days. When hOECs adopted their normal morphology on 5th day, they were harvested and placed in cultures with investigated biomaterials in 24-well plates at concentration of $1 \times 10^5$ cells per well.

Abdominal subcutaneous fat tissue samples (~5 g biopsies) were placed into HBSS supplemented with 1% antibiotic-antimycotic solution (penicillin/streptomycin/amphotericin B solution, Sigma Aldrich) and washed extensively. Tissue fragments were cut into pieces using surgical scissors and then digested with 1 mg/mL collagenase type I for 40 minutes at 37° C. in $CO_2$ incubator. Obtained suspension was centrifuged at 1200×g for 10 minutes. The supernatant was discarded, while pellet of cells was re-suspended in CGM and transferred to a culture flask. Before the experiment cells were passaged and transferred to 24-well plates coated with investigated biomaterials. Seeding density was $3 \times 10^5$ cells per well.

The Characterization of hOECs and hASCs Phenotype

The identification of the cellular specific phenotype of hOECs and hASCs was performed after first passage, before the experiment of nanohydroxyapatite biocompatibility assessment. The phenotype of hOECs was characterized with immunofluorescence staining. For this purpose, cells were cultured on a 24-well plate, with seeding density of $2 \times 10^5$ cells per well. Cells' phenotype was assessed when the cultures reached 70% confluence. For analysis cells were fixed using 4% paraformaldehyde for 45 minutes in room temperature, washed three times with HBSS and permeabilized for 15 minutes with HBSS containing 0.05% Triton X-100 and 5% of bovine serum. Following permeabilization, the cultures were washed again using HBSS. The incubation with primary anti-body was performed in HBSS overnight at 4° C.

The following rabbit polyclonal antibodies were used to detect specific hOECs: anti nerve growth factor receptor (NGFR-p75); anti-glial fibrillary acidic protein (GFAP) and anti-s100. All antibodies derived from Abcam, and were used at dilution 1:1000. After specific staining, cells were washed with HBSS and incubated for 1.5 h in room temperature with secondary antibody in HBSS—goat anti-rabbit IgG conjugated with Atto448 (1:800 dilution). After specific staining cultures were counterstained with DAPI (1:1000). Observations of stained cultures were performed using an inverted microscope (Zeiss, Axio Observer A.1) and documented using a Power Shot digital camera (Canon). Human ASCs were characterized by immunophenotyping using fluorochrome conjugated monoclonal antibodies specific for CD34, CD45, CD90, CD73b and CD105 (all antibodies purchased from BD Pharmingen). Isotype-matched antibodies were used as controls. The procedure was performed as it was described previously. Briefly, before staining cells were washed with HBSS containing 2% FBS, and re-suspended at total of $3 \times 10^5$ cells/ml. Cells were incubated at 4° C. for 20 min with the specific antibodies preconjugated with allophycocyanin (APC), peridinin chlorophyll protein complex (PerCP), fluorescein isothiocyanate (FITC), or phycoerythrin (PE). At least ten thousand stained cells were acquired and analysed by Becton Dickinson FACS Calibur flow cytometer. The samples were analysed using FlowJo software (trial version). Additionally, multipotency of hASCs was evaluated by specific differentiation toward osteogenic, chondrogenic, and adipogenic precursors. For this purpose, cultures of hASCs were maintained in StemPro® differentiation media (Life Technologies), following manufacturer's instructions. In order to perform the test, the cells were seeded in a 24-well plate at the initial density of $3 \times 10^5$ per well. Culture media (500 µl/per well) were changed every two days. Cultures propagated in the CGM were used as a control to establish the effectiveness of the differentiation process. Differentiation of hASCs towards osteoblasts lasted 21 days, while into adipocytes and chondrocytes 14 days. After experiment osteogenic cultures were stained with Alizarin Red, chondrogenic with Safranin 0 and adipogenic with Oil Red 0. All staining procedures were performed accordingly to the manufacturer's protocols described previously [36]. Preparations were analysed using inverted microscope (Zeiss, Axio Observer A.1) and documented using a Power Shot digital camera (Canon).

The Proliferation Rate (PR), Morphology and Viability of hOECs and hASCs on nHAP Based Biomaterials Proliferative activity of hOECs and hASCs in cultures with the biomaterials was determined using resazurin based assay (TOX8, Sigma Aldrich). The test was performed at 24, 48 and 120 hour of hOECs and hASCs cultures. The dye was added to a CGM in amount equal to 10% of its volume. The cultures were incubated with the dye for 2 hours in a $CO_2$ incubator, then supernatants were collected, placed in 96-well plate and measured with microplate spectroscopic reader (BMG Labtech). Proliferation rate (PR) in hOECs and hASCs cultures with nHAP, nHAP: $Li^+$ and 5% addition of $Li^+$ was presented as absorbance read at 600 nm and 690 nm, including blank sample i.e. CGM incubated without cells. In order to evaluate the influence of europium-doped nHAP: $Li^+$ on hASCs metabolic activity the PR was presented as arbitrary unit—i.e. normative value evaluated with regards to cultures nHAP: $Li^+$[37].

The proliferative activity was also described with the population doubling time (PDT) parameter, determined using on-line calculator [38]. The calculated values were expressed in hours, reflecting time needed for hOBCs and hASCs to double their number since their inoculation on biomaterial. In case of hASCs cultures on europium-doped nHAP: $Li^+$ the PDT was correlated with PDT of cells propagated on nHAP: $Li^+$ and expressed as. The amount of cells was estimated based on the cells' growth curve designated during TOX8 test, performed at definite time intervals for cultures at propagated at density $1 \times 10^5$; $2 \times 10^5$; $3 \times 10^5$; $6 \times 10^5$; $9 \times 10^5$ and $12 \times 10^5$ cells per well.

The morphology, growth pattern, as well as cellular attachment of the cultures propagated on investigated biomaterials was observed under epifluorescence microscope and using scanning electron microscope (SEM). The observations were performed on cultures fixed with 4% paraformaldehyde. For fluorescence imaging cell cultures were stained with atto-565-labeled phalloidin for cytoskeleton visualization and counterstained using diamidino-2-phenylindole (DAPI). Both dyes were diluted 1:1000 in HBSS, the details of the staining procedure were described previously. Observations were performed using fluorescence inverted microscope (Axio Observer A1, Zeiss), while documentation of stained cultures were performed using a PowerShotCamera (Canon). The SEM imaging microphotographs were performed according to well established methodology published previously [39]. Cultures were analyzed using SE1 detector at 10 kV filament tension (SEM, Zeiss Evo LS 15) and 5000× magnification.

The cultures viability on biomaterials was investigated using a two-color fluorescence live/dead assay (Double Staining Kit, Sigma Aldrich). The staining procedure was performed in accordance to manufacturer's instructions.

OECs Gene Expression Analysis

Cells cultured on investigated materials were homogenized using TRI Reagent. Total RNA was isolated using the phenol-chloroform method. Quality and quantity of isolated total RNA were determined using nano-spectrometer (WPA Biowave II). Genomic DNA digestion and cDNA synthesis were performed using PrimeScript kit (Takara, Clontech). For each reaction, 500 ng of total RNA was used. Both processes were performed in accordance with the manufacturers' instructions using a T100 Thermal Cycler (Bio-Rad). The quantitative polymerase chain reaction (qPCR) reactions were performed using a CFX Connect™ Real-Time PCR Detection System (BioRad). Reaction mixture contained 2 µl of cDNA in a total volume of 20 µl using SensiFast SYBR & Fluorescein Kit (Bioline). The concentration of primers in each reaction equaled to 500 nM. Relative gene expression analysis (Qn) was calculated in relation to the GAPDH housekeeping gene (see Table 3).

Results and Discussion

Characterization of Cells Used in the Experiment

Figure 7:
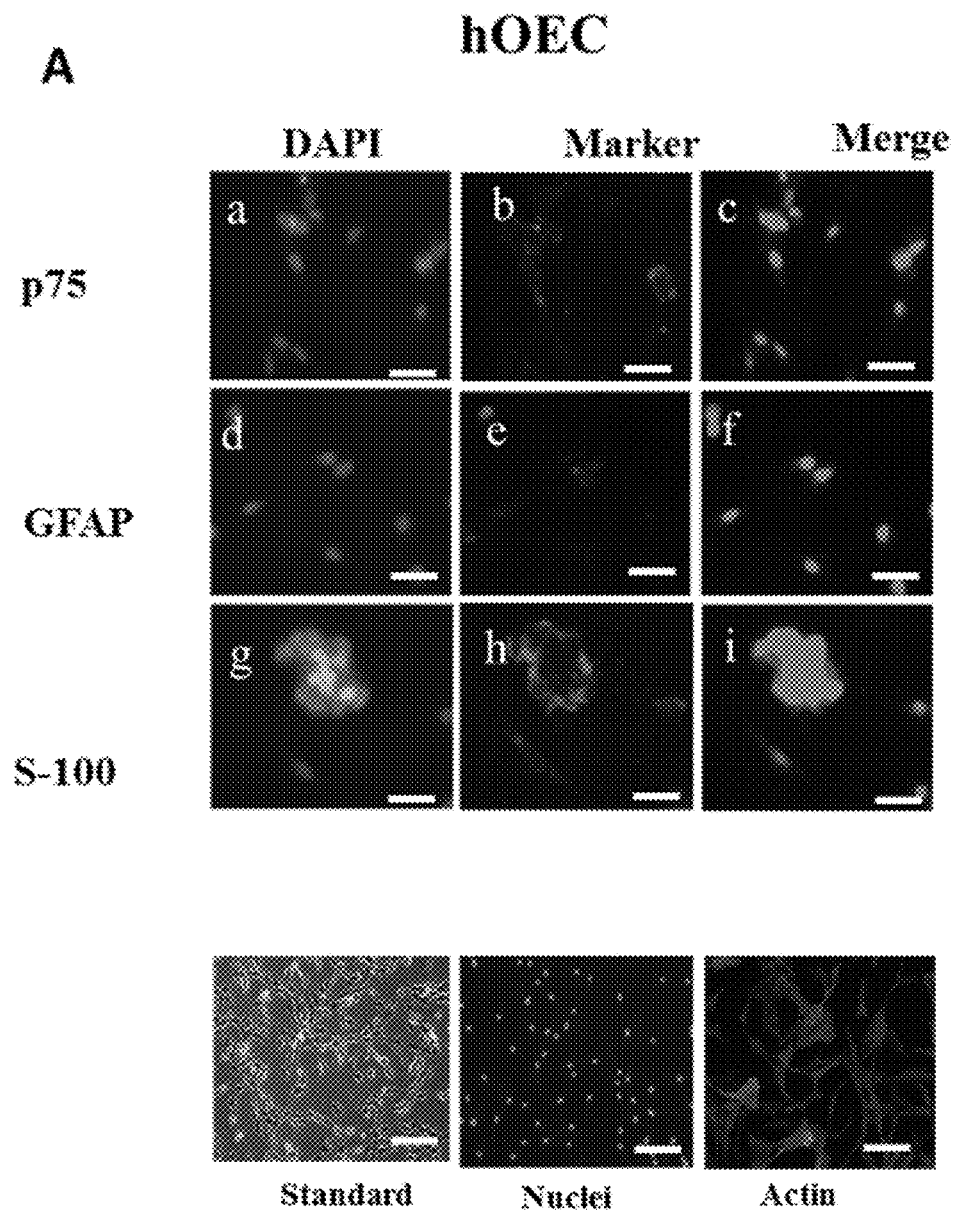
FIG. 7 presents The characteristics of hOECs and hASCs used for the experiment. (A) The hOECs expressed neuron-specific markers p75$^{NGF}$, GFAP and s-100. Additionally, the morphology of cells in cultures was shown. (B) The analysis of hASCs phenotype showed that obtained population was positive for CD44, CD73, CD90 and CD105 i.e. mesenchymal markers and did not expressed hematopoietic markers CD34 and CD45. The typical features of hASCs morphology in standard, adipogenic, osteogenic and chondrogenic cultures was shown. Characteristic features of differentiated hASC was revealed after specific staining—lipid-rich vacuoles in adipogenic cultures (Oil Red O), chondrogenic nodules (Sarfanin-O) and calcium deposits (Alizarin Red). The scale bar included in the pictures=100 μm.
Figure 7:
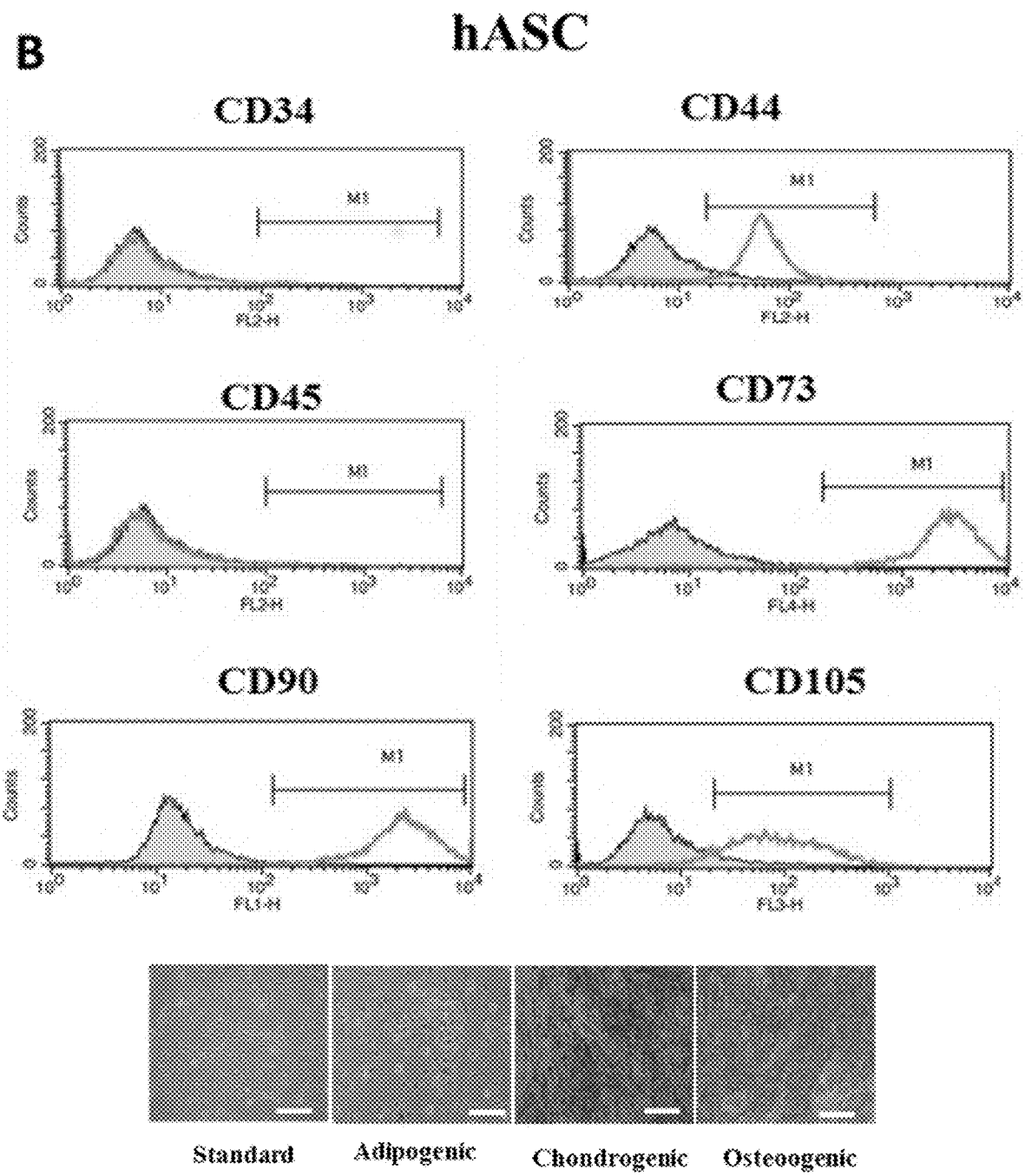

The specific phenotype of human OECs and ASCs used in this experiment was confirmed in the course of cellular immunophenotyping tests. We showed that population of hOECs express following markers: NGF-p75, GFAP and s-100 (FIG. 7A). Obtained results are in stands in good agreement with the previous observations regarding heterogeneity of OECs population, both antigenically and morphologically, showing that olfactory glia may be a source of progenitors both for astrocyte-like cells and Schwann cell-like cells. The denser immunoreactivity of investigated markers was noted perinuclear localization. The obtained hOECs morphologically shared features both of Schwanna and astrocyte-like cells (FIG. 6A). The population of isolated hASCs was defined by the criteria established by International Society of Cellular Therapy [40]. In cultures the cells were distinguished by the fibroblast-like morphology and exhibited ability for the adhesion. Specific markers of mesenchymal cells were detected (CD44, CD73, CD90, CD105), while the expression of markers of hematopoietic origin was not observed. Additionally, obtained hASCs differentiated into adipocytes, osteoblast and chondrocytes, respectively. The results of multipotency assay, along with characteristics of hASCs immunophenotype are presented in the FIG. 7B.

The Positive Influence of nHAP_Li$^+$ on Proliferative Activity of Progenitor Cells and their Viability Suppressing Apoptosis Via Down-Regulation of BAX/BCL-2 and Stabilization of p53/p21 Ratio.

TABLE 3

The list of used primers in the quantitative polymerase chain reaction (qPCR).

| Gene | Primer | Sequence 5'-3' | Loci | Ta [° C.] | Amplicon lenght [bp] | Accesion no. |
|---|---|---|---|---|---|---|
| Bax | Forward | ACCAAGAAGCTGAGCGAGTGTC | 235-256 | 59.6 | 365 | NM_001291428.1 |
|  | Reverse | ACAAAGATGGTCACGGTCTGCC | 627-648 |  |  |  |
| Bcl-2 | Forward | ATCGCCCTGTGGATGACTGAG | 1010-1030 | 58.6 | 129 | NM_000633.2 |
|  | Reverse | CAGCCAGGAGAAATCAAACAGAGG | 1115-1138 |  |  |  |
| p21 | Forward | AGAAGAGGCTGGTGGCTATTT | 21-41 | 57.9 | 169 | NM_001220777.1 |
|  | Reverse | CCCGCCATTAGCGCATCAC | 171-189 |  |  |  |
| p53 | Forward | AGATAGCGATGGTCTGGC | 868-885 | 57.8 | 381 | NM_001126118.1 |
|  | Reverse | TTGGGCAGTGCTCGCTTAGT | 1229-1248 |  |  |  |
| GAPDH | Forward | GTCAGTGGTGGACCTGACCT | 894-913 | 59.1 | 256 | NM_001289746.1 |
|  | Reverse | CACCACCCTGTTGCTGTAGC | 1130-1149 |  |  |  |

Confocal Microscopy

Preparations were observed using the Live Imager (Zeiss) confocal microscope with spinning disk (Yokogawa CSU-X1A 500) using the 405 nm laser (Colibri). Samples were observed using 20× (NA=0.4 LD) objective, images were captured with EMCCD (QImaging Rolera EM-C2) camera. Collected z-stacks were merged using orthogonal projection mode.

Statistical Analysis

All experiments were triplicated. The analysis of data obtained in biological assays were analyzed with STATISTICA 10.0 software (StatSoft, Inc., Statistica for Windows, Tulsa, Okla., USA). The normality of the population data was determined using Shapiro-Wilk test, while equality of variances was assessed by Levene's test. Differences between groups were determined using one- or two-way analysis of variance (ANOVA).

Olfactory ensheathing glial cells belong to the cell population, that have limited proliferative potential and viability that strongly limited their clinical application, in turn the adipose-derived multipotent stromal cells exhibit great proliferative potential and prolonged lifespan in long-term cultures [41].

The phenotypic plasticity of OECs and ASCs, contributes to the fact that their growth and secretory activity strongly depend on the type of microenvironment, regulating their cytophysiology and influencing survival both, in vitro and in vivo. Thus, application of particular biomaterial designed as a carrier for progenitor cells, and dedicated to the nerve tissue regeneration requires possessing specific features. First of all, from neurosurgical point of view—relatively simple physical form of carrier, that would improve transplantation procedure, and second of all highly bio-reactive platform, that would enhance proliferation rate of cells, thus influencing on functionality of progenitor cell-based therapy. Here, we have found that proposed nHAP:Li$^+$ fulfilled these criteria.

Figure 8:
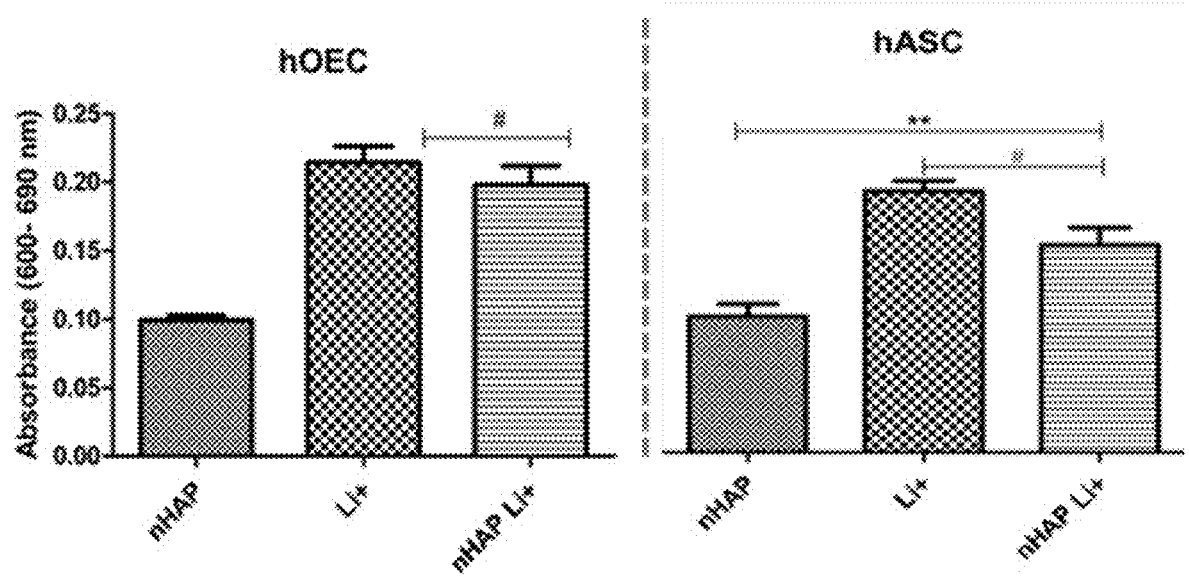
FIG. 8 presents the proliferative activity of hOECs and hASC cultured on nHAP, nHAP:Li$^+$ and with Li$^+$ addition after 24 h (A:D1), 72 h (B:D3), 120 h (C:D5) and results of population doubling time analysis (D). The statistically significant differences associated with increased proliferative activity were indicated with an asterisk (*??<0.05; ??<0.01; *??<0.001), while related to the decrease with hashtag ($^\#$??<0.05; $^{\#\#}$?<0.01; $^{\#\#\#\#}$??<0.001).
Figure 8:
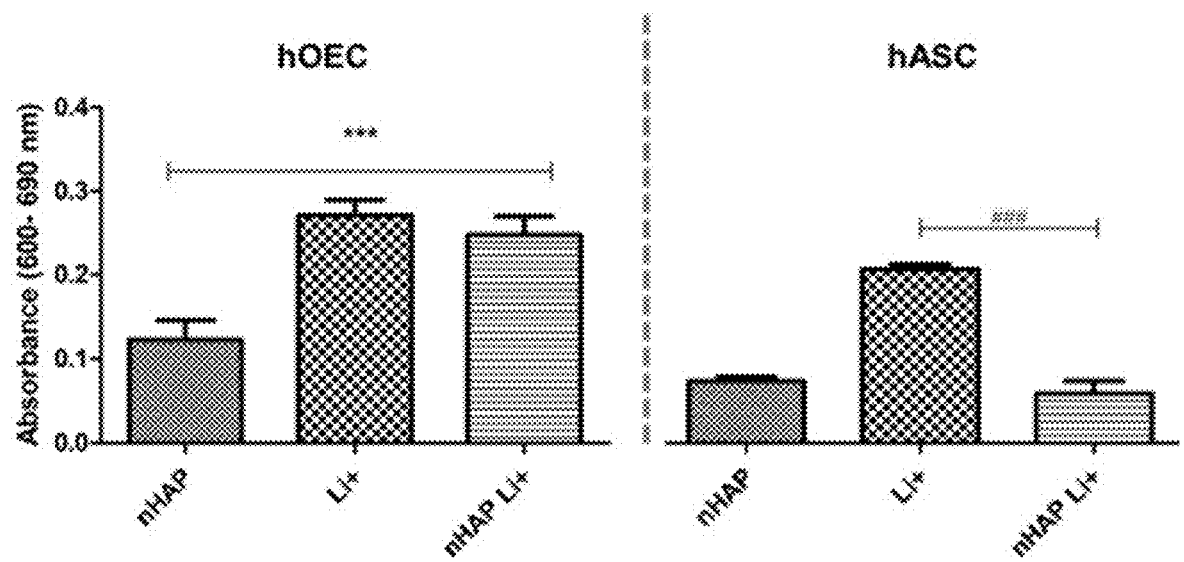
Figure 8:
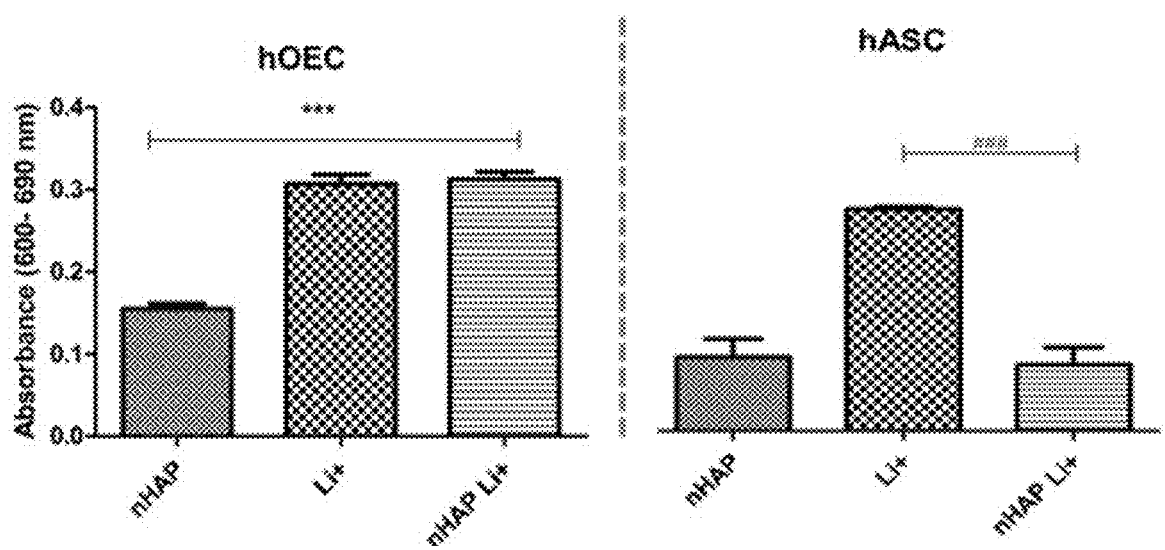
Figure 8:
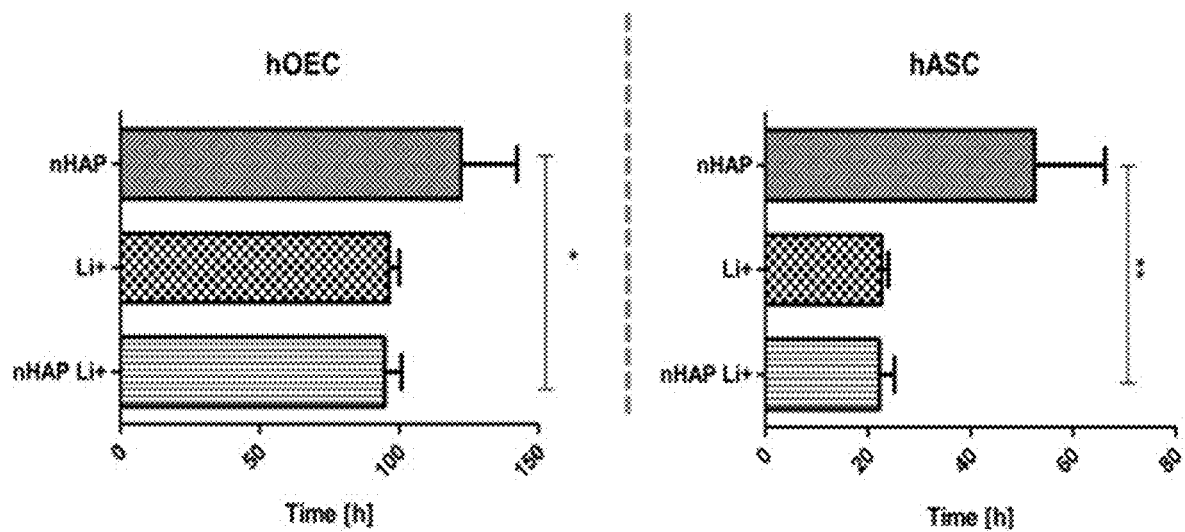

In order to determine the specific effect of nHAP:Li$^+$ on cytophysiology of hOECs and hASCs, we evaluated individual effect of nHAP and Li$^+$ ions addition onto the cultures. The results of the analysis was shown in the FIG. 8. We observed that proliferation activity of hOECs propagated on nHAP:Li$^+$ was improved when compared to the cultures on nHAP without the Li$^+$ incorporation. The increase of the hOECs proliferative activity in cultures on nHAP:Li$^+$ maintained throughout the test, similarly to the hOECs activity in cultures with Li$^+$ ions. In turn the acceleration of hASCs proliferation in cultures on nHAP:Li$^+$ was observed only during the first 24 hours of the test, in the adaptive phase of cells growth. However, both in case of hOECs and hASCs the time required for population doubling of cultures on nHAP:Li$^+$ had shortened in relation to the cultures on nHAP. Additionally, the results obtained for cultures on nHAP: Li$^+$ closely corresponded with the PDT determined in cultures with lithium alone. This strongly indicates on pro-proliferative influence of lithium on cells activity, and corresponds with previous studies showing that neural progenitor cells [42,43] and multipotent stromal cells [12] treated with Li$^+$ exert higher proliferative capacity.

Furthermore, the high proliferative state of hOECs and hASCs cultures on nHAP: Li$^+$, corresponded with their high viability. The percentage of dead cells in nHAP:Li$^+$ cultures was significantly lower than in cultures on nHAP (see FIG. 8). Cytoprotective effect of lithium was associated with its anti-apoptotic properties. The lithium was shown to increase the expression of anti-apoptotic molecule—B-cell lymphoma protein-2 (Bcl-2) and suppress the expression of pro-apoptotic genes: Bax and p53. This mechanism of lithium action was defined as a prominent in neuroprotection against excitotoxicity [44].

Bearing in mind, mentioned above reports we decided to investigate the influence of lithium doped in nHAP on mRNA level of Bax, Bcl-2, p53 and p21 genes. Our results showed that the Bax/Bcl-2 ratio in hOECs is comparable in all investigated culture. The Bax/Bcl-2 index indicates on increased transcript levels of Bax, however the difference between Bax and Bcl-2 level are not statistically significant. The mRNA level for p53 was statistically increased in hOECs cultures with lithium, when compared with cultures on nHAP and nHAP:Li$^+$. Moreover the lowest p53/p21 ratio indicating on constitutive level of these transcript was noted just in hOECs propagated on nHAP:Li$^+$. The results considering the expression profile of apoptotic pathway genes obtained for hOECs are consistent with those determined on hASCs. The significant decrease of Bax expression was noted in nHAP:Li$^+$ and the p53/p21 ratio was established suggesting that nHAP:Li$^+$ did not alter its transcript level (see FIG. 9).

Figure 9:
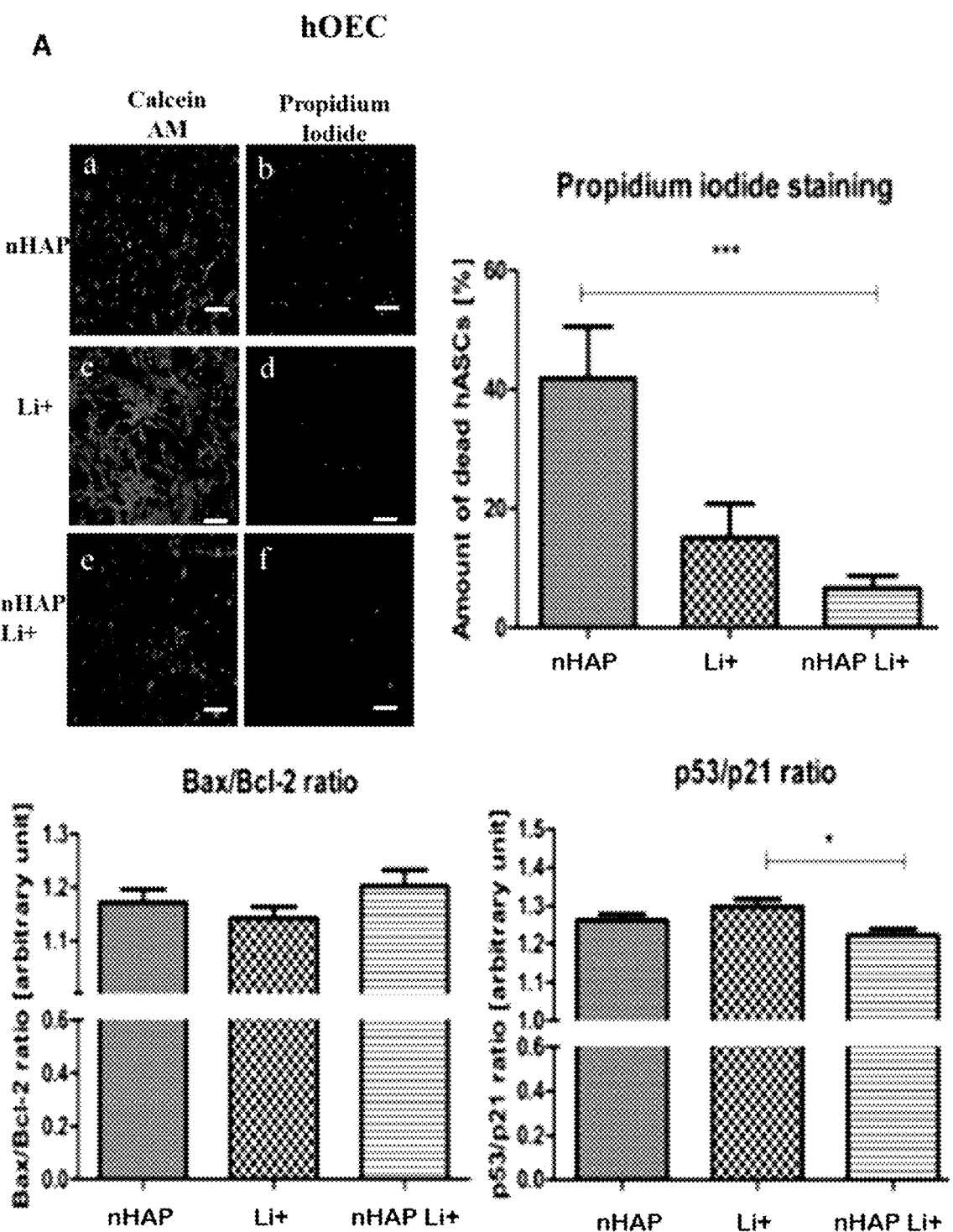
FIG. 9 presents the influence of nHAP:Li on hOECs (A) and hASCs (B) viability. The images from the epifluorescent microscope were prepared using 100× magnification (scale bar=100 μm). The viable cells are green stained (visualized with calcien-AM), while dead cells are stained with propidium ioide (red-stained cells). The quantitative analysis of images was performed using ImageJ software (NIH). The differences in transcripts level was determined using qRT-PCR technique. The results were presented as ratio of interested genes. The transcript level of genes was normalized to the reference gene expression (GAPDH). The statistically significant differences were indicated with an asterisk (*??<0.05; ??<0.01; *??<0.001).
Figure 9:
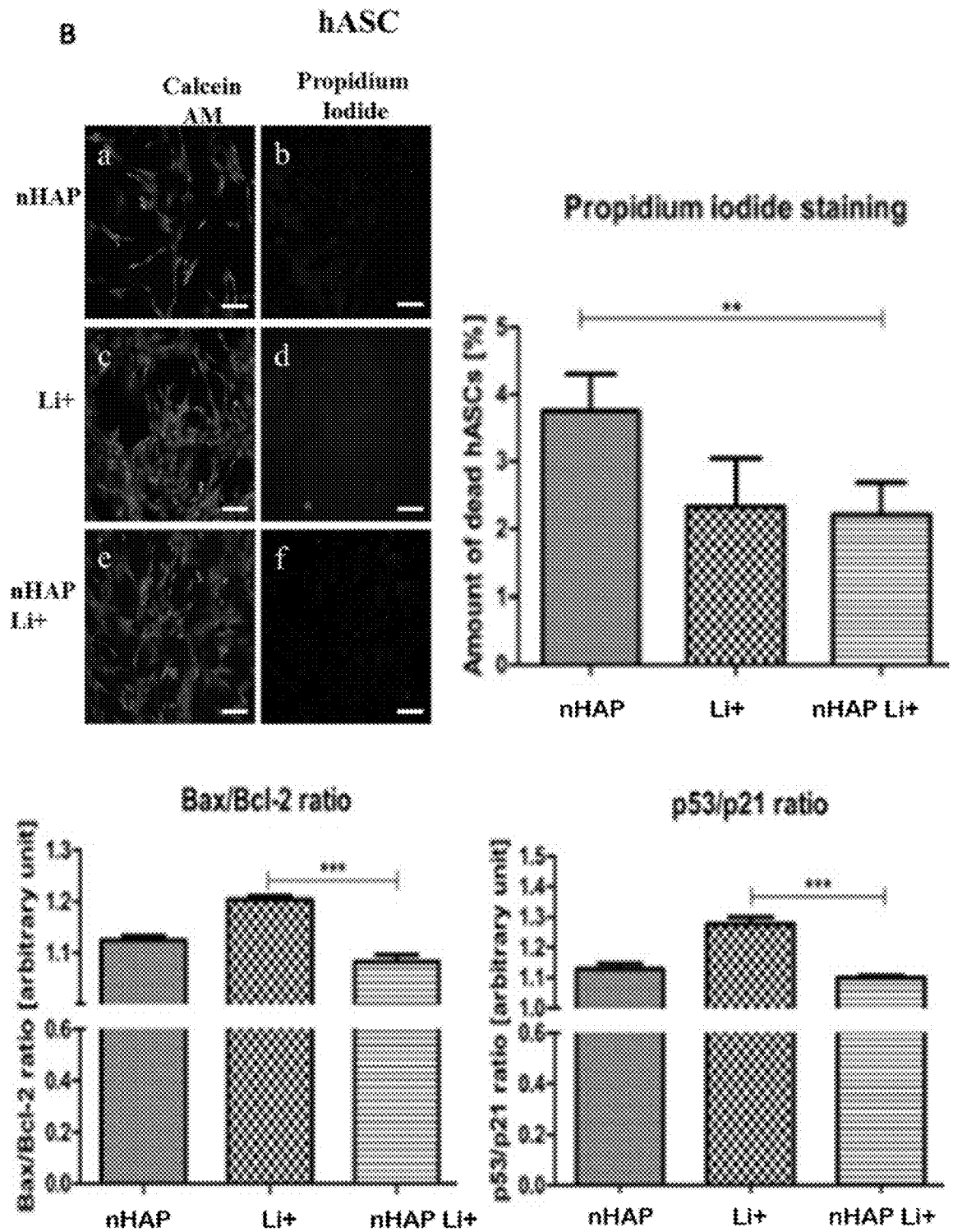

Obtained results indicate that in terms of anti-apoptotic properties lithium, released form nHAP as well as added to the culture environment, has convergent effect on progenitor cells, both derived from olfactory bulb and from adipose tissue (FIG. 9).

Figure 10:
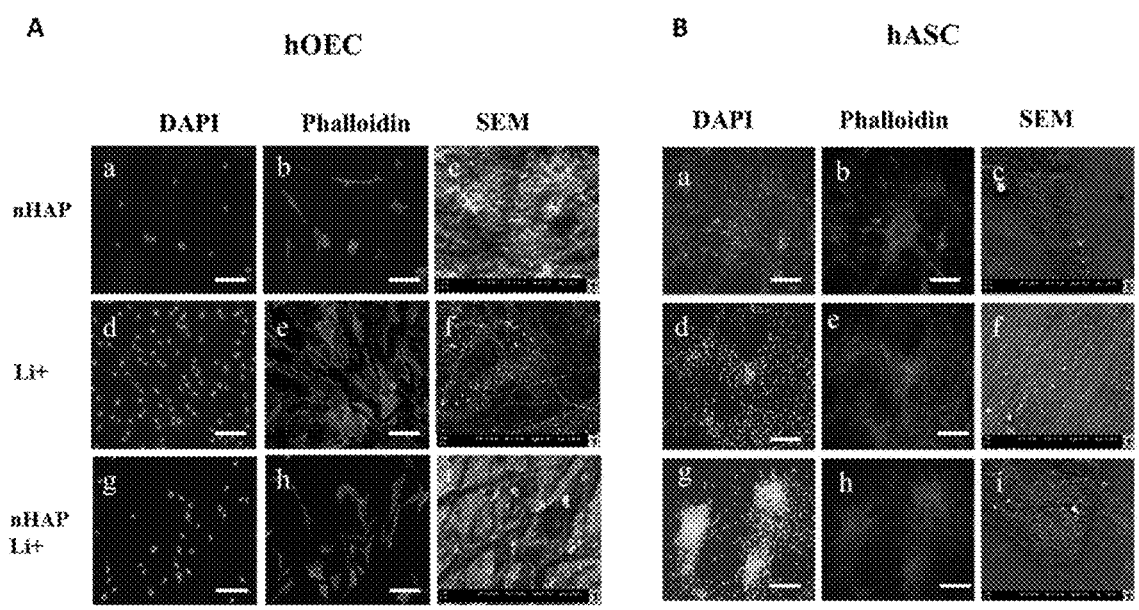
FIG. 10 presents the morphology and growth pattern of hOECs and hASC cultures with investigated biomaterials (nHAP and nHAP:Li$^+$) and Li$^+$ addition. Scale bars presented in the images obtained using epifluroescent microscope are equal 100 μm, while scale bars in the microphotographs from SEM are equal 2 μm.

Next, to the influence on nHAP: Li$^+$ on cells proliferation an viability, we determined the role of biomaterial topography on the cells morphology and spreading (FIG. 10). The observations made with epifluorescent microscope and SEM brought the undisputable evidence, on lithium role in maintaining proper morphology of investigated progenitor cells. Both hOECs and hASCs expressed better adhesion and spreading with their characteristic morphologies on nHAP:Li$^+$ biomaterials than nHAP. Obtained results corresponds with the results of proliferation test, and suggest that Li released form nHAP and introduced directly to the culture has beneficial effect on hOECs and hASCs, although growth pattern of cultures on nHAP:Li$^+$ differed when compared to cultures with Li$^+$ ions. The hOECs propagated on nHAP:Li$^+$ had proper morphology of neural nature, and covered the surface area more loosely than cultures with Li$^+$ ions, and did not developed tight intracellular junctions. In turn, the hASCs in cultures with nHAP:Li$^+$ formed cellular aggregates, thus it seems that nHAP:Li$^+$ promoted not only cell-biomaterial interactions, but also initiated cell-cell contact in hASCs cultures. Indeed, lithium was proposed as a factor for inducing neural differentiation of MSCs [12]. Cell aggregation is associated with progression of progenitor cells in differentiation. It was shown that aggregate cultures of progenitor cells recapitulates crucial physical aspects of the cellular development, including cell-cell interactions that mediate also proliferation and apoptosis [45,46].

In general, our results seems to confirm the trend presented in literature about pro-proliferative and anti-apoptotic effects of lithium on progenitor cells, the novel aspect of this study is however the delivery method of Li$^+$ ions, based on application of nHAP scaffolds. Presented concept was also investigated by the Wang et al., however in the context of possible use of Li-doped hydroxyapatite scaffolds for bone regeneration. Therefore, it seems that increased bioactivity of nHAP:Li$^+$ may find various application in regenerative medicine.

nHAP: Li as a Potential Theranostic Agent/Vesicle—the Biocompatibility Analysis Using hASCs The high biocompatibility of nHAP:Li$^+$, showed using hOECs as well as hASCs in vitro model, prompt us to use this scaffold as a platform for highly luminescent of europium (III) ions. Bearing in mind convergent cellular response on nHAP:Li$^+$, the evaluation of biological properties of nHAP:Li$^+$ co-doped with Eu$^{3+}$ ions was performed on cells exhibiting greater proliferation potential and cellular plasticity i.e. hASCs.

Figure 11:
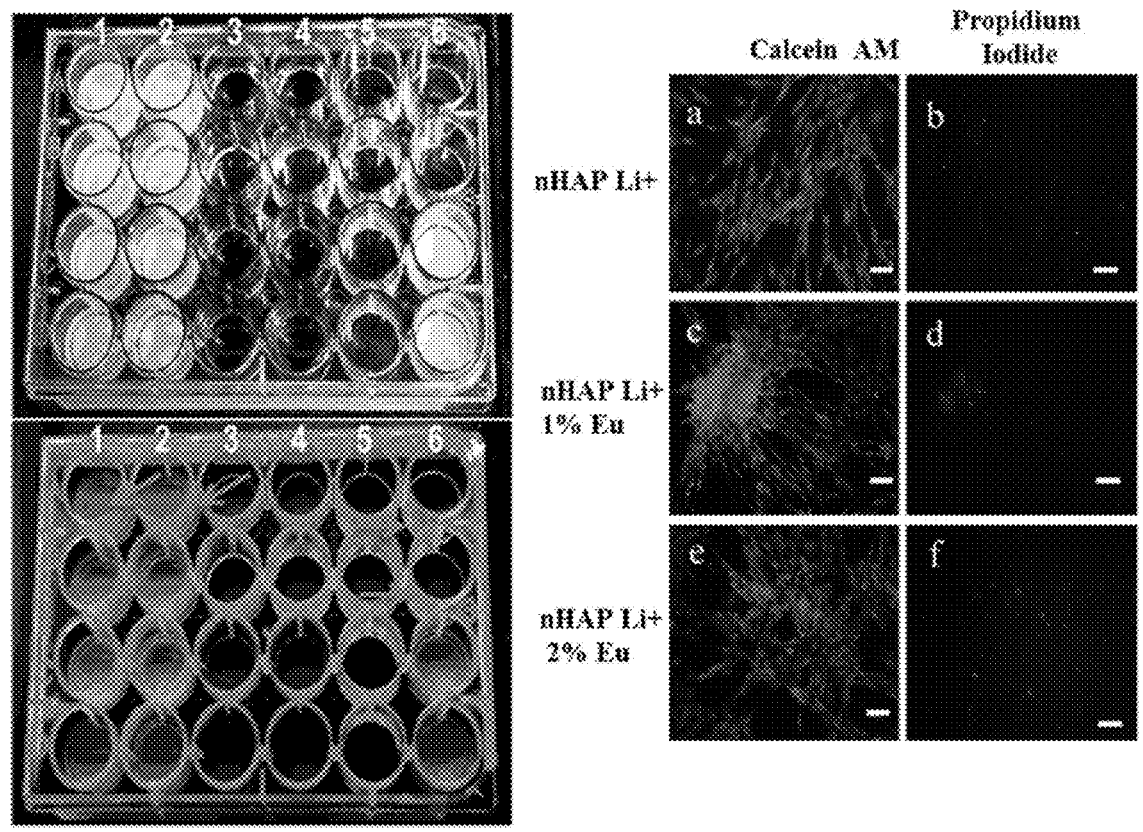
FIG. 11 presents the results of biocompatibility analysis of nHAP:Li$^+$ doped with europium(III). Culture dish—images of the nanohydroxyapatites (nHAP—1A, 2 A) doped with Li+ (2 mol % Li$^+$:nHAP—1B, 2 B) and co-doped with Eu$^{3+}$ ions (5% mol Li$^+$, x % mol Eu$^{3+}$:nHAP, where x is 1 (1C, 2C, 5C and 6C), x is 2 (1D, 2D, 5D and 6D)) combined with human adipose derived stromal steam cells and control sample (3A-D and 4A-D) without excitation (on top) as well as disc and UV-irradiation (on bottom). Images from the epifluorescent microscope presents results of live/dead staining. Percentage of dead cells stained with propidium ioide was determined and low expression of pro-apoptotic genes was noted. Confocal microscope revealed the internalization of Eu$^{3+}$ ions in cells cytoplasm and in the perinuclear region. Cells propagated on investigated were also characterized by increased proliferative activity. The statistically significant differences between proliferation activity of cultures on nHAP:Li$^+$ doped with Eu$^{3+}$ ions and nHAP: Li$^+$ were indicated with a hashtag (#??<0.05; ##??<0.01; ###??<0.001), while between 1 mol % Eu$^{3+}$ and 2 mol % Eu$^{3+}$ with an asterisk.
Figure 11:
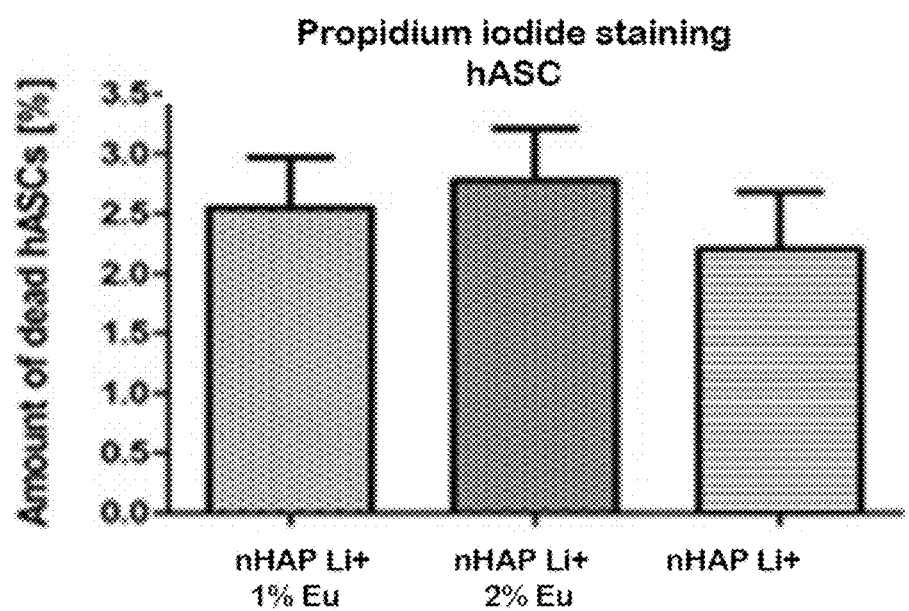
Figure 11:
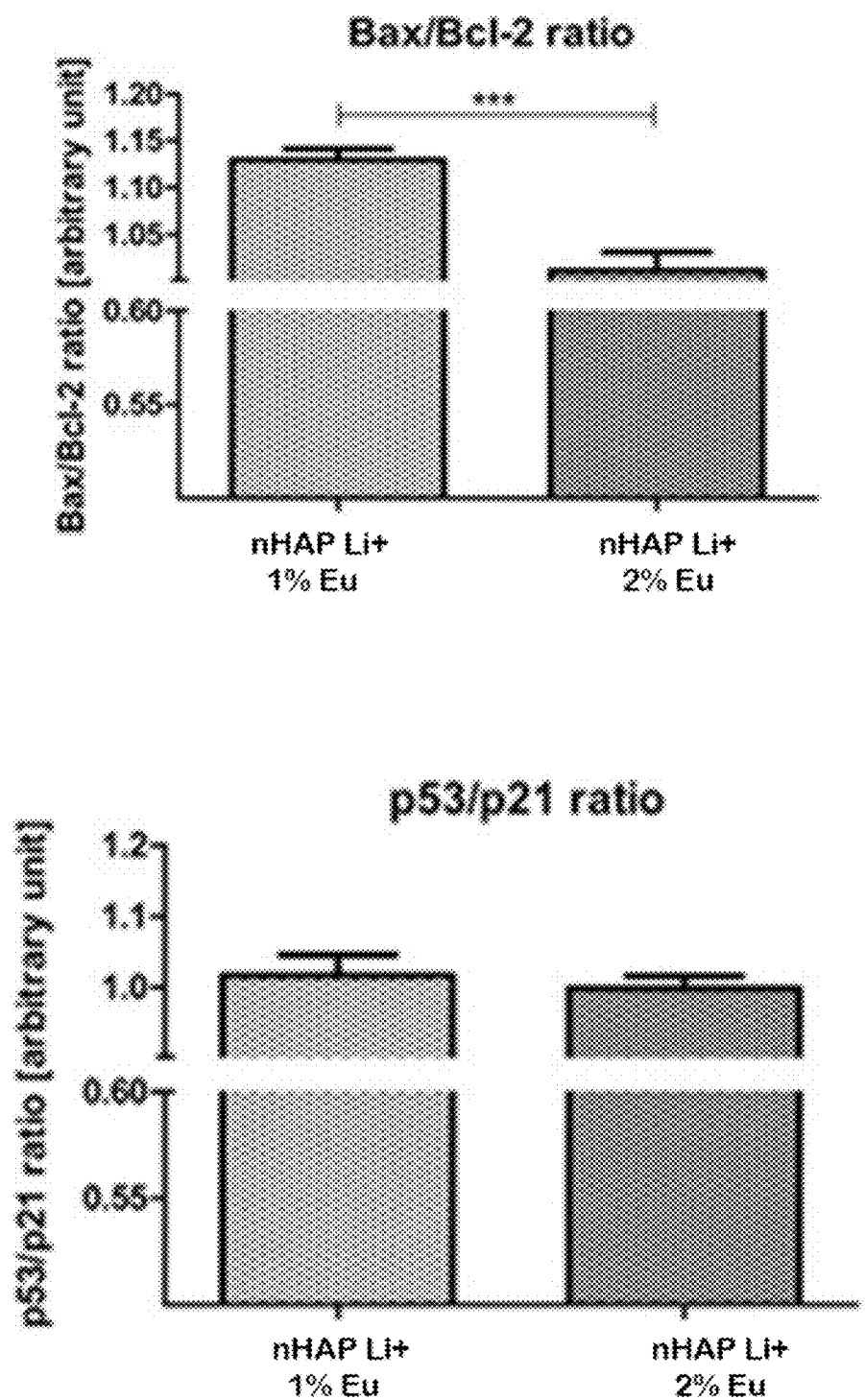
Figure 11:
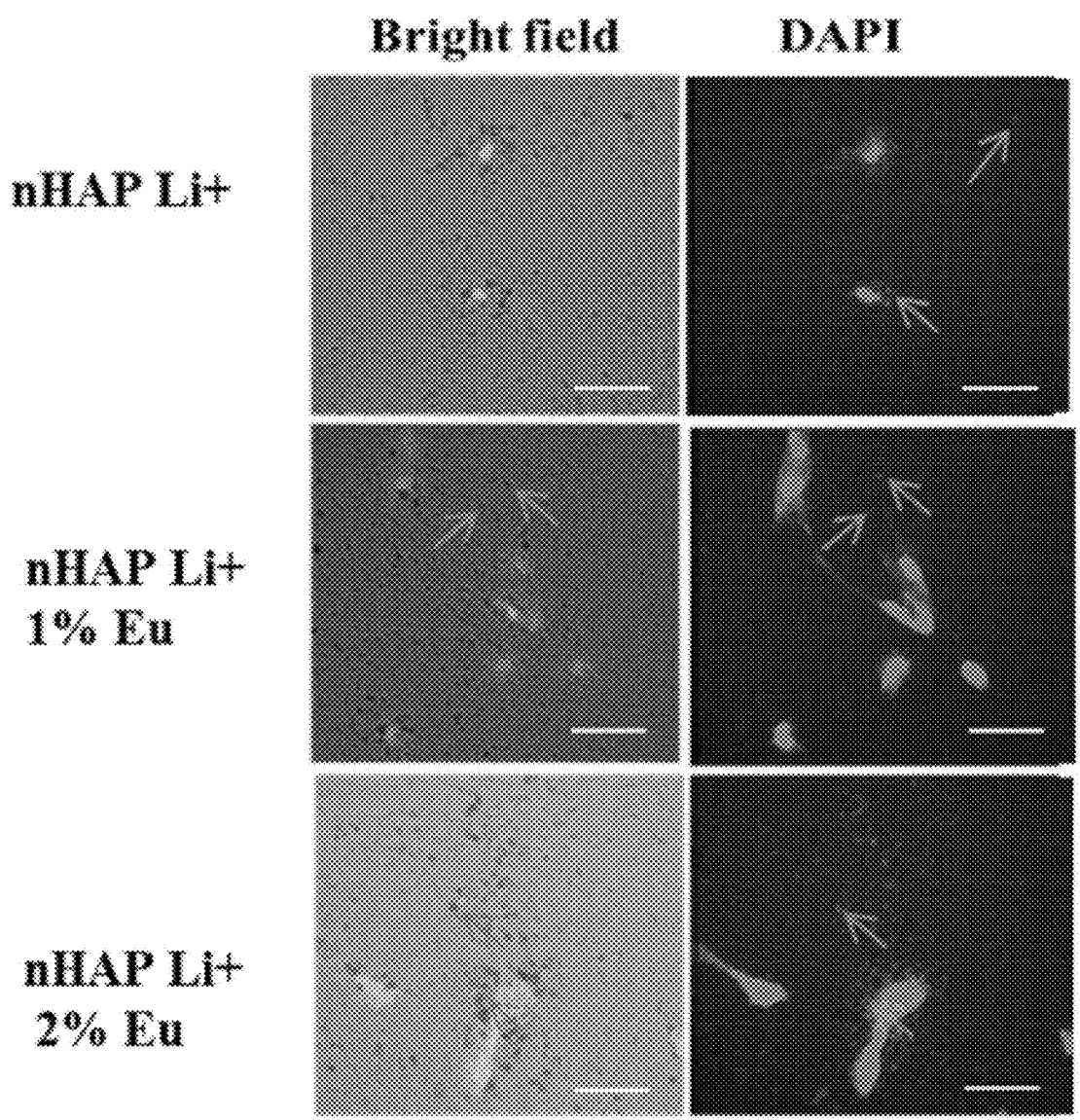
Figure 11:
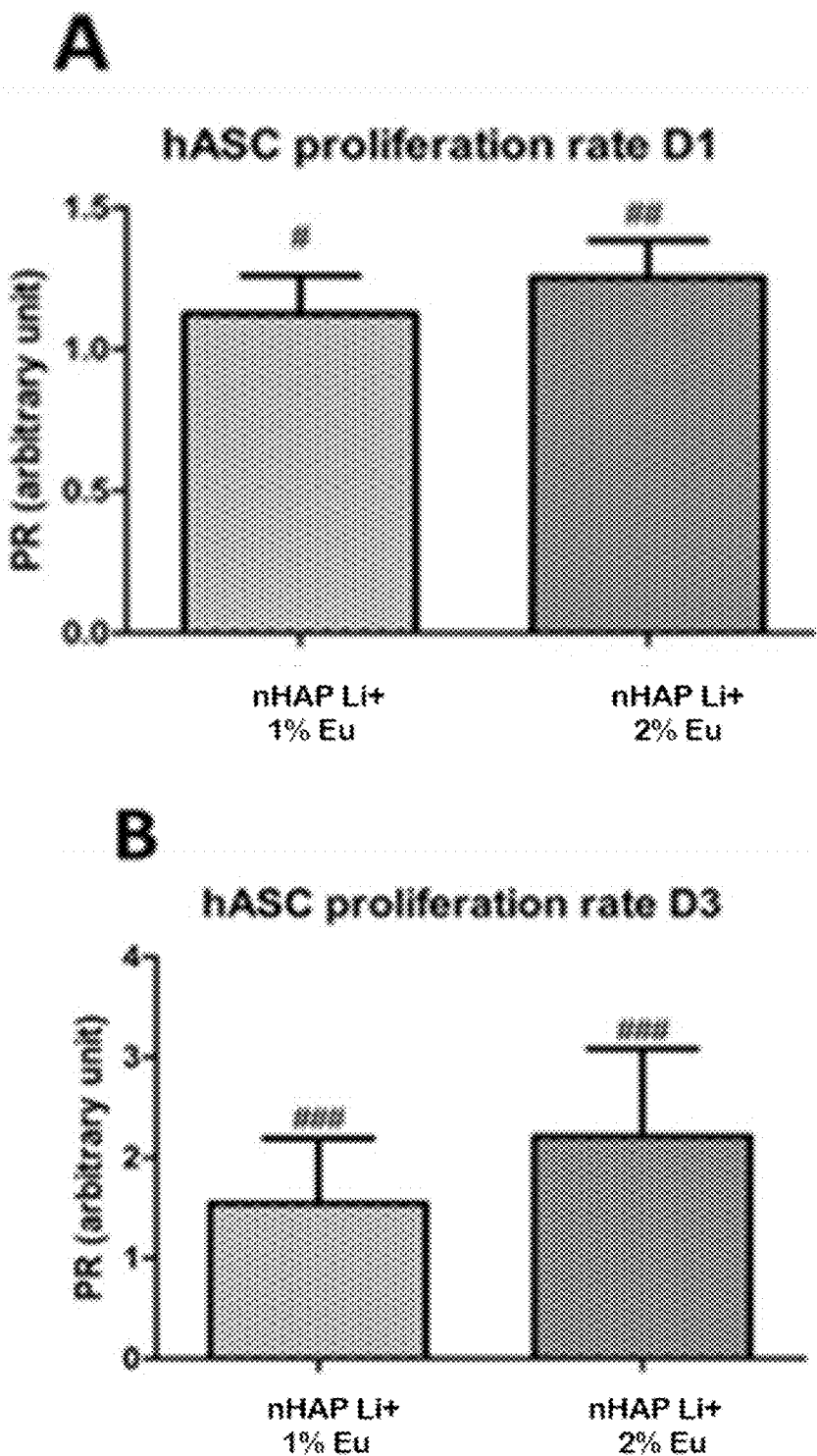
Figure 11:
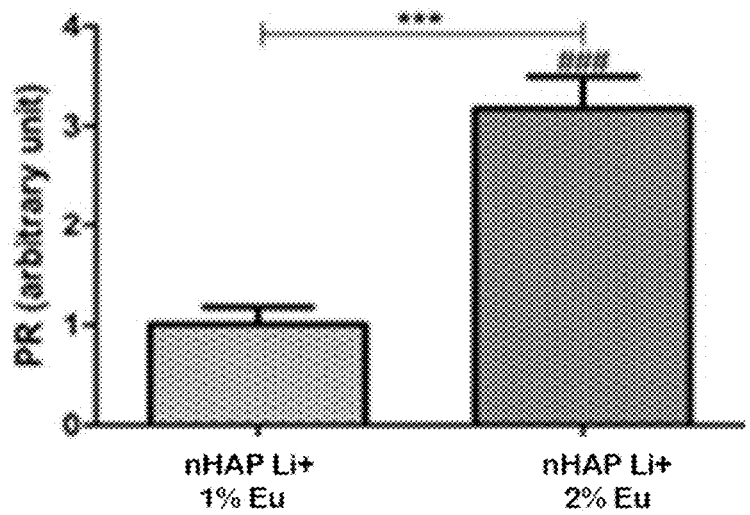
Figure 11:
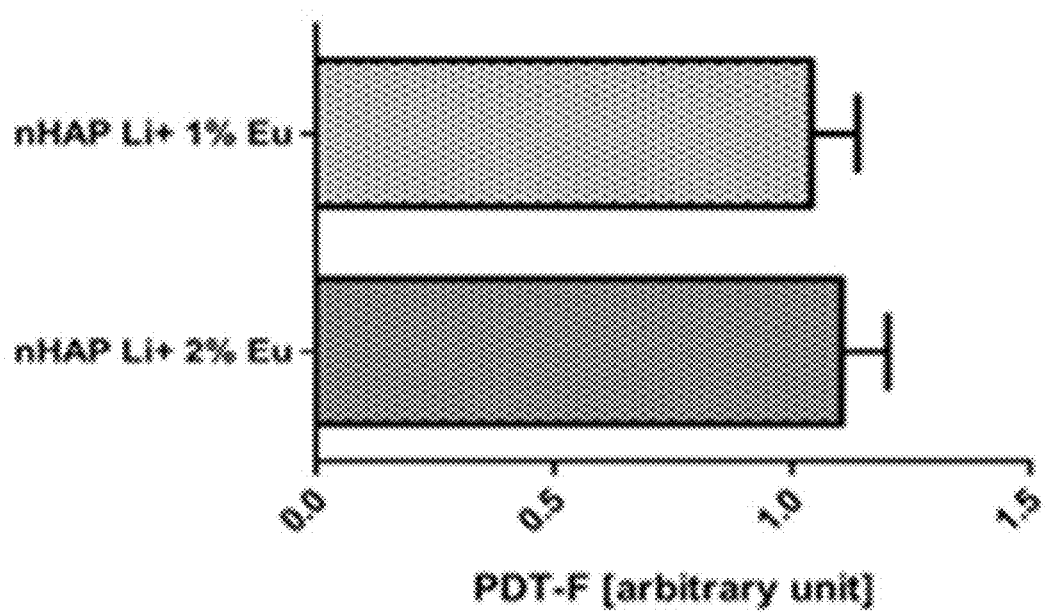

The analysis of proliferation activity of hASCs (see FIG. 11) showed that Eu$^{3+}$ ions addition increased proliferation rate significantly regardless to its concentration (1 mol % or 2 mol %) during the first third days of test, but after 5 days of culture, the increased cellular activity was maintained in cultures with 2 mol % of Eu$^{3+}$ ions. Nevertheless, the incorporation of Eu$^{3+}$ ions had no significant effect on population doubling time, when compared with hASCs cultures on nHAP:Li$^+$. Further, the addition of Eu$^{3+}$ ions had also no significant influence on loss of cellular viability. The hASCs propagated on nHAP:Li$^+$ co-doped with Eu$^{3+}$ ions exhibited even more enhanced tendency for aggregation, therefore the slight increase in percentage of dead-cells may results from increased PI reaction within aggregates. Our results suggest, that the nHAP:Li$^+$ co-doped with Eu$^{3+}$ ions has gain increased anti-apoptotic properties. The Bax/Bcl-2 ratio significantly decreased in cultures on nHAP:Li$^+$ co-doped with 2 mol % Eu$^{3+}$ ions. Additionally, the results of p53/p21 ratio determination indicates on stability in those transcript levels. The analysis of cellular internalization showed perinuclear and cytoplasmic localization.

Obtained results indicate on great possibility of nHAP:Li$^+$ application for theranostic usage in regenerative medicine, especially taking into account its potential to increase survival of progenitor cells [47] that can differentiate into neural lineage. Our concept fits in with the current trends used for spinal cord injuries treatment i.e. developing and seeking for effective cell-based delivery strategies, biomolecule delivery strategies as well as scaffold-based therapeutic strategies [48].

REFERENCES

[1] Bracken, M. B., Shepard, M. J.; Collins, W. F., Jr.; Holford, T. R.; Baskin, D. S.; Eisenberg, H. M.; Flamm, E.; Leo-Summers, L.; Maroon, J. C.; Marshall, L. F. Methylprednisolone or naloxone treatment after acute spinal cord injury: 1-year follow-up data. Results of the second National Acute Spinal Cord Injury Study. J. Neurosurg. 76 (1992) 23-31.

[2] Bracken, M. B., Shepard, M. J., Holford, T. R., Leo-Summers, L., Aldrich, E. F., Fazl, M., Fehlings, M. G., Herr, D. L., Hitchon, P. W., Marshall, L. F., Nockels, R. P., Pascale, V., Perot, Jr., P. L., Piepmeier, J., Sonntag, V. K., Wagner, F., Wilberger, J. E., Winn, H. R., Young, W. Methylprednisolone or tirilazad mesylate administration after acute spinal cord injury: 1-year follow up. Results of the third National Acute Spinal Cord Injury randomized controlled trial. J. Neurosurg. 89 (1998) 699-706.

[3] Chou, R. H., Lu, C. Y., Wei-Lee, Fan, J. R., Yu, Y. L., Shyu, W. C. The potential therapeutic applications of olfactory ensheathing cells in regenerative medicine. Cell Transplant. 23 (2014) 567-571.

[4] Grosu-Bularda A., Manea C., Lascar I. The role of olfactory ensheating cells in regenerative medicine: review of the literature. Rom. J. Rhinol. 5 (2015) 75-80.

[5] Dasari, V. R., Veeravalli, K. K. and Dinh D. H., Mesenchymal stem cells in the treatment of spinal cord injuries: A review, World J. Stem Cells 6 (2014) 120-133.

[6] Tabakow, P., Jarmundowicz, W., Czapiga, B., Fortuna, W., Miedzybrodzki, R., Czyz, M., Huber, J., Szarek, D., Okurowski, S., Szewczyk, P., Gorski, A., Raisman, G. Transplantation of Autologous Olfactory Ensheathing Cells in Complete Human Spinal Cord Injury. Cell Transplantation. 22 (2013) 1591-1612.

[7] Lu, J., Féron, F., Mackay-Sim, A., Waite, P. M. E. Olfactory ensheathing cells promote locomotor recovery after delayed transplantation into transected spinal cord. Brain. 125 (2002) 14-21.

[8] Li, J., Lepski, G. Cell transplantation for spinal cord injury: a systematic review. Biomed. Res. Int. 2013 (2013) 786475.

[9] Imaizumi, T., Lankford, K. L., Waxman, S. G., Greer C. A., Kocsis J. D. Transplanted olfactory ensheathing cells remyelinate and enhance axonal conduction in the demyelinated dorsal columns of the rat spinal cord. J. Neuroscience. 18 (1998) 6176-6185.

[10] Moore T. J. and Abrahamse H., Neuronal Differentiation of Adipose Derived Stem Cells: Progress So Far, Int. J. Pharm. 2014 (2014) ID 827540.

[11] Bae K. S., Park J. B., Kim H. S., Kim D. S., Park D. J., Kang S. J., Neuron-like differentiation of bone marrow-derived mesenchymal stem cells, Yonsei. Med. J. 52 (2011) 401-142.

[12] Ivanov, S. Y., Mukhametshin, R. F., Muraev, A. A., Solodkaya, D. V. Synthetic materials used for the substitution of bone defects. Annals of Oral & Maxillofacial Surgery. 1 (2013) 1-4.

[13] Ferraz, M. P., Monteiro, F. J., Manuel, C. M. Hydroxyapatite nanoparticles: A review of preparation methodologies. J. Appl. Biomater. Biomech. 2, (2004) 74-80.

[14] Liu, H., Webster, T. J. Nanomedicine for implants: a review of studies and necessary experimental tools. Biomater. 28 (2007) 354-369.

[15] Chandra A., Singh K., Singh S., Sivakumarb S. and Patra A. K., A luminescent europium(III)-platinum(II) heterometallic complex as a theranostic agent: a proof-of-concept study, Dalton Trans., 45 (2016) 494-497.

[16] Venkatesan J., Lowe B., Anil S., Kim S. K., Shim M. S., Combination of NanoHydroxyapatite with Stem Cells for Bone Tissue Engineering, J. Nanosci. Nanotechnol., 16 (2016) 8881-8894.

[17] Dong, B.-T., Tu, G.-J., Han, Y.-X., Che, Y. Lithium enhanced cell proliferation and differentiation of mesenchymal stem cells to neural cells in rat spinal cord. Int. J. Clin. Exp. Pathol. 8 (2015) 2473-2483.

[18] Hashimoto, R., Senatorov, V., Kanai, H., Leeds, P., Chuang, D. M. Lithium stimulates progenitor proliferation in cultured brain neurons. Neuroscience. 117 (2003) 55-61.

[19] Wang, W., Shi, D, Lian, J., Guo, Y., Liu, G., Wang, L., Ewing, R. C. Luminescent hydroxylapatite nanoparticles by surface functionalization. Appl. Phys. Lett. 89 (2006) 183106.

[20] Yang, P., Quan, Z., Li, C. Kang, X., Lian, H., Lin, J. Bioactive, luminescent and mesoporous europium-doped hydroxyapatite as a drug carrier. Biomater. 29 (2008) 4341-4347.

[21] Queiroz, A. C., Santos, J. D., Monteiro, F. J., Gibson, I. R., Knowles, J. C. Adsorption and release studies of sodium ampicillin from hydroxyapatite and glass-reinforced hydroxyapatite composites. Biomater. 22 (2001) 1393-1400.

[22] K. Ravindranadh, B. Babu, V. Pushpa Manjari, G. Thirumala Rao, M. C. Rao, R. V. S. S. N. Ravikumar, J. Lumin., 159 (2015) 119

[23] Martin P., Carlot G., Chevarier A., Den-Auwer C., Panczer G., Mechanisms involved in thermal diffusion of rare earth elements in apatite, J. Nuclear. Mater. 275 (1999) 268-276.

[24] Su H., Chu T. H., Wu W., Lithium enhances proliferation and neuronal differentiation of neural progenitor cells in vitro and after transplantation into the adult rat spinal cord, Exp. Neurol. 206 (2007) 296-307.

[25] Sandhöfer B., Meckel M., Delgado-López J. M., Patricio T., Tampieri A., Rösch F. and Iafisco M., Synthesis and preliminary in vivo evaluation of well-dispersed biomimetic nanocrystalline apatites labeled with positron emission tomographic imaging agents, ACS Appl. Mater. Interfaces, 7 (2015) 10623-10633.

[26] Rietveld, H. M., A profile refinement method for nuclear and magnetic structures. J. Appl. Cryst. 2 (1969) 65-71.

[27] Wiglusz, R. J., Bednarkiewicz, A., Lukowiak, A. Synthesis and optical properties of Eu3+ ion doped nanocrystalline hydroxyapatites. Spectr. Lett. 43 (2010) 333-342.

[28] Rietveld, H. M., A profile refinement method for nuclear and magnetic structures. J. Appl. Cryst. 2 (1969) 65-71.

[29] Destainville, A., Champion, E., Bernasche-Assollant, D., Laborde, E. Synthesis, characterization and thermal behavior of apatitic tricalcium phosphate. Mater. Chem. Phys. 80 (2003) 269-277.

[30] Abdulrahman, I., Tijani, H. I., Mohammed, B. A., Saidu, H., Yusuf, H., Jibrin, M. N., Mojammed, S. From Garbage to Biomaterials: An Overview on Egg Shell Based Hydroxyapatite. J. Mater. 2014 (2014) 802467

[31] Gibson I. R., Bonfield W. Novel synthesis and characterization of an AB-type carbonate-substituted hydroxyapatite. J. Biome. Res. 59 (2002) 697-708.

[32] Kokubo, T., Kim, H. M., Kawashita, M., Novel bioactive materials with different mechanical properties. Biomater. 24 (2003) 2161-2175.

[33] Kovaleva, E. S., Shabanov, M. P., Putlyaev, V. I., Tretyakov, Y. D., Ivanov, V. K., Silkin, N. I. Bioresorbable carbonated hydroxyapatite Ca10-xNax(PO4)6-x(CO3)x(OH)2 powders for bioactive materials preparation. Cent. Eur. J. Chem. 7, (2009) 168-174.

[34] Filippov, Y. Y., Klimashina, E. S., Ankudinov, A. B., Putlayev, V. I., Carbonate substituted hydroxyapatite (CHA) powder consolidated at 450° C., J. Phys Conf. Series. 291 (2011) 012036.

[35] Grzesiak, J., Fryczkowski, R., Lis, A., Szarek, D., Laska, J., Marycz, K. Characterization of Olfactory Ensheathing Glial Cells Cultured on Polyurethane/Polylactide Electrospun Nonwovens. Int. J. Polym. Sci. 2015 (2015) 908328.

[36] Marycz K., Kornicka K., Basinska K. and Czyrek A., Equine metabolic syndrome affects viability, senescence, and stress factors of equine adipose-derived mesenchymal stromal stem cells: New insight into EqASCs isolated from EMS horses in the context of their aging, Oxid. Med. Cell. Longev. 2016 (2016) ID 4710326.

[37] Glant, T. T., Jacobs, J. J., Molnar, G., Shanbhag, A. S., Valyon, M., Galante, J. O., Bone resorption activity of particulate-stimulated macrophages. J. Bone Min. Res. 8 (1993) 1071-1079.

[38] http://www.doubling-time.com/compute.php.

[39] Grzesiak, J., Marycz, K., Szarek, D., Bednarz, P., Laska, J. Polyurethane/polylactide-based biomaterials combined with rat olfactory bulb-derived glial cells and adipose-derived mesenchymal stromal cells for neural regenerative medicine applications. Mater. Sci. Eng. C52 (2015) 163-170.

[40] Dominici, M.; Le Blanc, K.; Mueller, I.; Slaper-Cortenbach, I.; Marini, F.; Krause, D.; Deans, R.; Keating, A.; Prockop, D.; Horwitz, E. Minimal criteria for defining multipotent mesenchymal stromal cells. The International Society for Cellular Therapy position statement. Cytotherapy 2006, 8, 315-317

[41] Mayeur, A., Duclos, C., Honoré, A., Gauberti, M., Drouot, L., do Rego J.-C., Bon Mardion, N., Jean, L., Vérin, E., Emery, E., Lemarchant, S., Vivien, D., Boyer, O., Marie, J.-P., Guérout, N., Potential of olfactory ensheathing cells from different sources for spinal cord repair. PLoS One. 8 (2013) e62860.

[42] Zanni G., Di Martino E., Omelyanenko A., Andang M., Delle U., Elmroth K. and Blomgren K., Lithium increases proliferation of hippocampal neural stem/progenitor cells and rescues irradiation-induced cell cycle arrest in vitro, Oncotarget. 6 (2015) 37083-37097.

[43] Yoneyama M., Shiba T., Hasebe S., Umeda K., Yamaguchi T. and Ogita K., Lithium promotes neuronal repair and ameliorates depression-like behavior following trimethyltin-induced neuronal loss in the dentate gyrus, PLoS One. 9 (2014) e87953.

[44] Chen R. W., Chuang D. M., Long term lithium treatment suppresses p53 and Bax expression but increases Bcl-2 expression. A prominent role in neuroprotection against excitotoxicity, J Biol Chem. 274 (1999) 6039-6042.

[45] Ghasemi-Mobarakeh L., Prabhakaran M. P., Tian L., Shamirzaei-Jeshvaghani E., Dehghani L. and Ramakrishna S., Structural properties of scaffolds: Crucial parameters towards stem cells differentiation, World J. Stem Cells. 7 (2015) 728-744.

[46] Tchao J., Han L., Lin B., Yang L. and Tobita K., Combined biophysical and soluble factor modulation induces cardiomyocyte differentiation from human muscle derived stem cells, Sci. Rep. 4 (2014) 6614-6625.

[47] Kempen P. J., Greasley S., Parker K. A., Campbell J. L., Chang H.-Y., Jones, 4 Robert Sinclair J. R., Gambhir S. S. and Jokerst J. V., Theranostic mesoporous silica nanoparticles biodegrade after pro-survival drug delivery and ultrasound/magnetic resonance imaging of stem cell, Theranostics. 5 (2015) 631-642.

[48] Tsintou M., Dalamagkas K. and Seifalian A. M., Advances in regenerative therapies for spinal cord injury: a biomaterials approach, Neural Regen Res. 10 (2015) 726-742.

---

The invention claimed is:

1. A method of manufacturing calcium nanohydroxyapatite ($Ca_{10}(PO_4)_6(OH)_2$) structurally modified with $Li^+$ ions to provide $Li_{0.1}Ca_{9.9}(PO_4)_6(OH)_2$, optionally doped with 1-2% mol of $Eu^{3+}$ cations, in a form of a nanocrystalline powder as a final product, comprising the following steps:

in a first step a solution of water soluble lithium nitrate is obtained by digestion of a stoichiometric amount of $Li_2CO_3$ in an excess of $HNO_3$;

in a second step, depending on the final product:

for $Li_{0.1}Ca_{9.9}(PO_4)_6(OH)_2$ as the final product, a solution of water soluble calcium nitrate is obtained by suspension of 73.35 g of $Ca(OH)_2$ in 200 ml of deionized water and subsequent digestion of calcium dioxide in an excess of 65% $HNO_3$ and 170 g of polyvinylpyrrolidone is added to form a solution of calcium nitrate and polyvinylpyrrolidone or, for $Li_{0.1}Ca_{9.9}(PO_4)_6(OH)_2$ doped with 1-2% mol of $Eu^{3+}$ cations as the final product, pure europium (III) nitrate is obtained by suspending stoichiometric amounts 0.0352 g of $Eu_2O_3$ in distilled water and subsequent digestion of europium oxide in an excess of 65% $HNO_3$ and subsequent three times re-crystallization, and a solution of 2.2434 g of $Ca(NO_3)_2.4H_2O$ dissolved in MQ-water is added to the pure europium (III) nitrate to obtain a solution of calcium nitrate and europium (III) nitrate;

in a third step an ammonium phosphate solution is obtained by dissolution of $(NH_4)_2HPO_4$ in water;

in a fourth step the solutions prepared in the first and second steps are added to the ammonium phosphate solution obtained in the third step to form a mixture, leading to fast precipitation of a by-product;

in a fifth step pH of the mixture is adjusted to 8-10 by addition of ammonium hydroxide $NH_4OH$ and the mixture is filtered under reduced pressure to obtain as a precipitate the by-product formed in the fourth step;

in a sixth step the precipitate resulting from the fifth step is washed 5 times and dried at 90° C. for 20-24 h; and in a seventh step the washed and dried precipitate resulting from the sixth step is subjected to a thermal treatment by gradually heating at 400-500° C. in air atmosphere for 3-4 hours, at a heating rate of 5° C. per minute to obtain the final product.

2. The method according to claim 1, wherein for manufacturing $Li_{0.1}Ca_{9.9}(PO_4)_6(OH)_2$ in the seventh step the precipitate resulting from the sixth step is subjected to a thermal treatment by gradually heating at 400° C. in air atmosphere for 4 hours, at a heating rate of 5° C. per minute to obtain the final product with a particle size distribution in the range of 30-50 nm and a surface area 40 $m^2/g$ or gradually heating at 500° C. in air atmosphere for 8 hours, at a heating rate of 20° C. per minute to obtain a particle size distribution in the range of 50-80 nm and a surface area 30 $m^2/g$.

3. The method according to claim 1 wherein for manufacturing $Li_{0.1}Ca_{9.9}(PO_4)_6(OH)_2$ doped with 1-2% mol of $Eu^{3+}$ in the seventh step the precipitate resulted in the sixth step is subjected to a thermal treatment by gradually heating at 500° C. in air atmosphere for 3 hours, at a heating rate of 5° C. per minute to obtain fine graded white powder with elongated rod shaped particles with mean particle size being of 80 nm length and 15 nm width.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Homo sapiens
<220> FEATURE:
<221> NAME/KEY: misc_feature
<223> OTHER INFORMATION: Bax Forward

<400> SEQUENCE: 1
accaagaagc tgagcgagtg tc                                           22

<210> SEQ ID NO 2
<211> LENGTH: 22
<212> TYPE: DNA
<213> ORGANISM: Homo sapiens
<220> FEATURE:
<221> NAME/KEY: misc_feature
<223> OTHER INFORMATION: Bax Reverse

<400> SEQUENCE: 2
acaaagatgg tcacggtctg cc                                           22

```
<210> SEQ ID NO 3
<211> LENGTH: 21
<212> TYPE: DNA
<213> ORGANISM: Homo sapiens
<220> FEATURE:
<221> NAME/KEY: misc_feature
<223> OTHER INFORMATION: Bcl-2 Forward

<400> SEQUENCE: 3
atcgccctgt ggatgactga g                                            21

<210> SEQ ID NO 4
<211> LENGTH: 24
<212> TYPE: DNA
<213> ORGANISM: Homo sapiens
<220> FEATURE:
<221> NAME/KEY: misc_feature
<223> OTHER INFORMATION: Bcl-2 Reverse

<400> SEQUENCE: 4
cagccaggag aaatcaaaca gagg                                         24

<210> SEQ ID NO 5
<211> LENGTH: 21
<212> TYPE: DNA
<213> ORGANISM: Homo sapiens
<220> FEATURE:
<221> NAME/KEY: misc_feature
<223> OTHER INFORMATION: p21 Forward

<400> SEQUENCE: 5
agaagaggct ggtggctatt t                                            21

<210> SEQ ID NO 6
<211> LENGTH: 19
<212> TYPE: DNA
<213> ORGANISM: Homo sapiens
<220> FEATURE:
<221> NAME/KEY: misc_feature
<223> OTHER INFORMATION: p21 Reverse

<400> SEQUENCE: 6
cccgccatta gcgcatcac                                               19

<210> SEQ ID NO 7
<211> LENGTH: 18
<212> TYPE: DNA
<213> ORGANISM: Homo sapiens
<220> FEATURE:
<221> NAME/KEY: misc_feature
<223> OTHER INFORMATION: p53 Forward

<400> SEQUENCE: 7
agatagcgat ggtctggc                                                18

<210> SEQ ID NO 8
<211> LENGTH: 20
<212> TYPE: DNA
<213> ORGANISM: Homo sapiens
<220> FEATURE:
<221> NAME/KEY: misc_feature
<223> OTHER INFORMATION: p53 Reverse

<400> SEQUENCE: 8
ttgggcagtg ctcgcttagt                                              20
```

```
<210> SEQ ID NO 9
<211> LENGTH: 20
<212> TYPE: DNA
<213> ORGANISM: Homo sapiens
<220> FEATURE:
<221> NAME/KEY: misc_feature
<223> OTHER INFORMATION: GADPH Forward

<400> SEQUENCE: 9
gtcagtggtg gacctgacct                                           20

<210> SEQ ID NO 10
<211> LENGTH: 20
<212> TYPE: DNA
<213> ORGANISM: Homo sapiens
<220> FEATURE:
<221> NAME/KEY: misc_feature
<223> OTHER INFORMATION: GAPDH Reverse

<400> SEQUENCE: 10
caccaccctg ttgctgtagc                                           20
```